Figure 4:
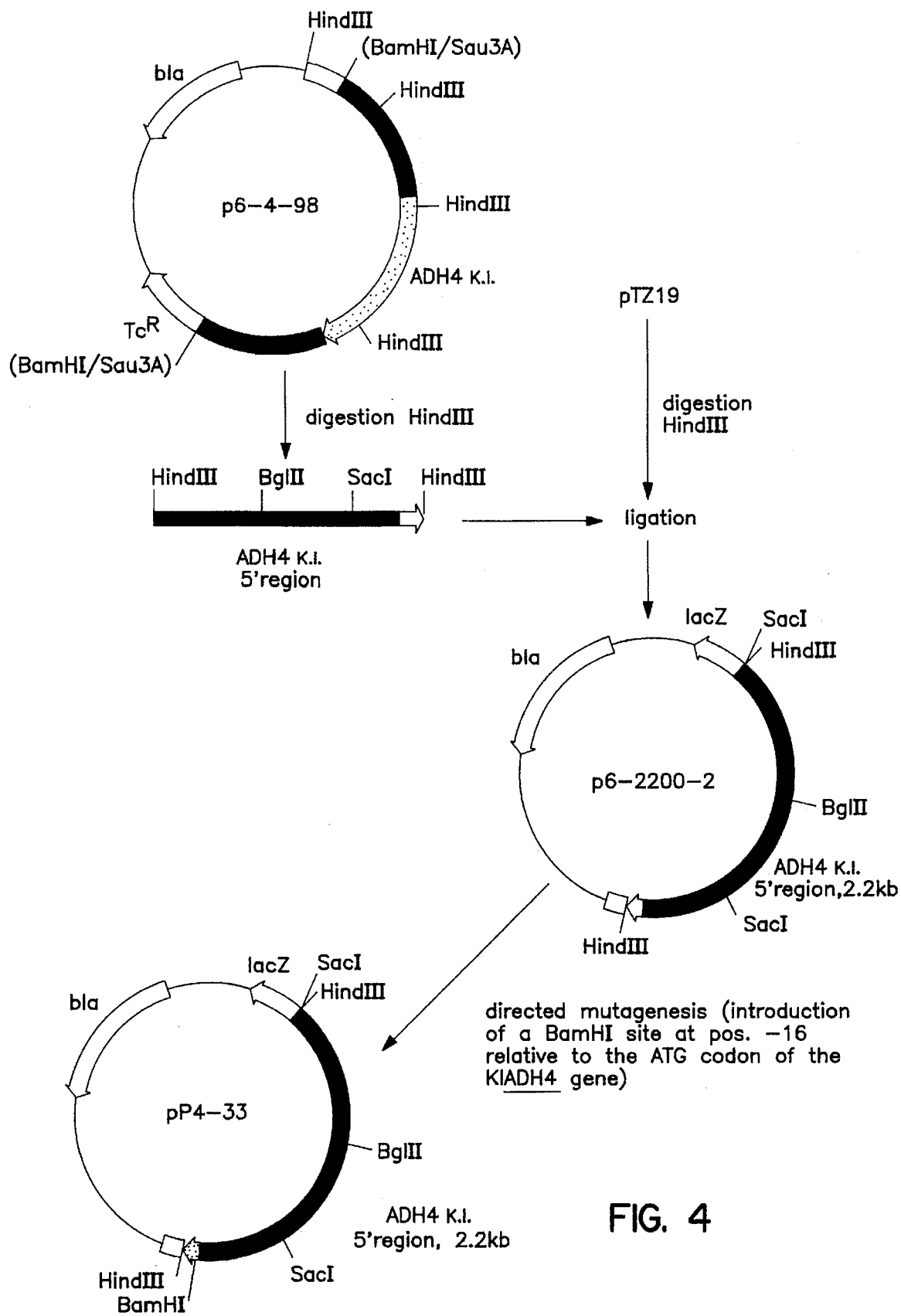

United States Patent [19]
Falcone et al.

[11] Patent Number: 5,627,046
[45] Date of Patent: May 6, 1997

[54] YEAST PROMOTER AND ITS USE

[75] Inventors: Claudio Falcone, Rome, Italy; Reinhard Fleer, Bures sur Yvette, France; Michele Saliola, Rome, Italy

[73] Assignee: Rhone-Poulenc Rorer S.A., Antony, France

[21] Appl. No.: 196,178

[22] PCT Filed: Aug. 19, 1992

[86] PCT No.: PCT/FR92/00803

§ 371 Date: Feb. 22, 1994

§ 102(e) Date: Feb. 22, 1994

[87] PCT Pub. No.: WO93/04176

PCT Pub. Date: Mar. 4, 1993

[30] Foreign Application Priority Data

Aug. 21, 1991 [FR] France ................................. 91 10476

[51] Int. Cl.⁶ .......................... C12N 15/11; C12P 21/02
[52] U.S. Cl. ..................... 435/69.1; 536/23.1; 536/24.1
[58] Field of Search .................... 435/69.1, 69.6, 435/69.9, 254.2, 320.1, 240.2, 240.4; 536/23.1, 24.1

[56] References Cited

U.S. PATENT DOCUMENTS

| | | | |
|---|---|---|---|
| 4,859,596 | 8/1989 | Hollenberg et al. | 435/172.3 |
| 5,017,478 | 5/1991 | Cashion et al. | 435/69.1 |
| 5,037,744 | 8/1991 | Knapp et al. | 435/69.6 |

OTHER PUBLICATIONS

Saliola et al., *Yeast*, vol. 7, Jun. 1991, pp. 391–400.
Bianchi et al. (1991), Curr. Genet. 19(3), 155–162.
Gould et al. (1989) PNAS, USA 86, 1934–1938.
Knight et al. (1985) EMBO J. 4, (8), 2093–2099.
Saliola et al. (1990) Yeast 6, 193–204.
Santanglo et al. (1988) Molec. Cell. Biol. 8(10), 4217–4224.
Wasylyk (1988) Biochem. Biophys Acta 951, 17–35.

*Primary Examiner*—Mindy Fleisher
*Assistant Examiner*—James Ketter
*Attorney, Agent, or Firm*—Julie K. Smith; Rosanne Goodman; Martin F. Savitzky

[57] ABSTRACT

DNA sequences comprising all or part of the ADH4 gene promoter of *K. lactis* or a derivative of the latter, and having transcriptional promoter activity. The invention also concerns the use of said sequences for the expression of recombined genes.

27 Claims, 15 Drawing Sheets

```
             |   10       |   20       |   30       |   40       |   50       |   60
   1   AGATCTATCA  ACGGCTACTA  ATAGAAGTTC  AACACCCAGA  AATTGATTGT  TTTGGCCTGA    60
  61   AATGTTAATG  GCAGGGAATC  AAGTATGAAG  TATGAAGTAT  GAAGTGTGAA  GTGTGAATCC   120
 121   CGTAAAATCG  GAGAAACATG  TGGTCACCTG  GTCAAGGACT  TAAGGGAACA  CAGCGGTTGT   180
 181   TCTCGGCATT  AAGCGGTACT  ATTGTCACTT  TGTAATGGCA  GTCCGAATCA  CGTTTTATTA   240
 241   TATGGGGGGG  GGGAAGGAAC  GACGGTACAT  AAGAATGAGG  GGCTTGGTTG  CGGTGTACGG   300
 301   GTTTAGTACC  CCTCTCGTCC  GTGCAAGCCC  AAAGACAAGT  TTTTGTTTCT  TTTTCGTATC   360
 361   CATCCCCAGA  ACAGTGCGCA  GCAAGGAAAT  ATTCCGTCAT  GCGTTTGGAT  GGTTTTTCCC   420
 421   CTATTGAGGG  GCAAGTGAGG  GGTAAACGAA  CGGCGCCTGA  AATTTTCCCG  CTCAATGATA   480
 481   TGAATAATCA  GTAGGATCTC  CGAGTTTCGC  AAGAAGCAGT  AAGCAACTCC  GTTTATTGC    540
 541   GAGACAACAC  TATTGTGAGA  AAAGGCACTC  AAAAAGCGAC  CTCCGTTAAT  TGATGTCAAC   600
 601   TGGCATCAAT  TTGAGATACT  TTGGGTCAAT  TTGCAGTGTG  CATTCGCATT  CTTTGTGTTA   660
 661   AAATCCTTTT  CCCCAGAAGT  CGGAGTTTAC  AGGACACAGG  GTGTGGAGCA  ATTGGGAGAG   720
 721   CTCCAGCAGG  GCTGGAGCTC  TGCCTCTGCC  TCTGCCCCAG  GTCCAGGTCC  AAGTCCAAGT   780
 781   CCAGGTCCAG  CGAGAACCGG  AGTGAGAGGT  GTGTGCTGTG  CCTTCCACTA  AACGAACCAG   840
 841   TATCCCAGGT  CTCTTAAGTT  TCCCAAATCT  CGGCATGGTC  AGGCCTCTCC  ACTGTAGCAG   900
 901   CCGCAGCACA  TTTTTTTTTT  TTTTCTCTCT  TCTAATGGAT  CAAGCATCAC  TACTTATCAC   960
 961   AATTTATCAC  TTTTTCCAAT  GATGTTGCCA  TTGCCCTTGT  TGGCCTTCTC  GAACTAGTCC  1020
1021   GTCTTTCTGG  TTTAACTTGG  TGAGGGAAAT  TCTTAGCACT  GGACTGCGCT  GTGATATGAC  1080
1081   CTGTTAAATT  ATAACAAGGA  GTCGTTTTTC  AATTGACAAT  TTCTTATCAT  TGTCTCTGGG  1140
1141   ATCAATTGGT  TTTTCTTCCT  CTCTTTCGCT  TTTCTCCCCC  ACCAACAACA  CAACATACAA  1200
1201   CACACGCAAT  G                                                          1211
             |   10       |   20       |   30       |   40       |   50       |   60
```

FIG. 1

```
      |  10       |  20       |  30       |  40       |  50       |  60
  1 GAGCTCTGCC TCTGCCTCTG CCCCAGGTCC AGGTCCAAGT CCAAGTCCAG GTCCAGCGAG  60
 61 AACCGGAGTG AGAGGTGTGT GCTGTGCCTT CCACTAAACG AACCAGTATC CCAGGTCTCT 120
121 TAAGTTTCCC AAATCTCGGC ATGGTCAGGC CTCTCCACTG TAGCAGCCGC AGCACATTTT 180
181 TTTTTTTTTT CTCTCTTCTA ATGGATCAAG CATCACTACT TATCACAATT TATCACTTTT 240
241 TCCAATGATG TTGCCATTGC CCTTGTTGGC CTTCTCGAAC TAGTCCGTCT TTCTGGTTTA 300
301 ACTTGGTGAG GGAAATTCTT AGCACTGGAC TGCGCTGTGA TATGACCTGT TAAATTATAA 360
361 CAAGGAGTCG TTTTTCAATT GACAATTTCT TATCATTGTC TCTGGGATCA ATTGGTTTTT 420
421 CTTCCTCTCT TTCGCTTTTC TCCCCCACCA ACAACACAgg atcc                  464
      |  10       |  20       |  30       |  40       |  50       |  60
```

FIG. 2

```
      |  10       |  20       |  30       |  40       |  50       |  60
  1 gtcgacGCGA GACAACACTA TTGTGAGAAA AGGCACTCAA AAAGCGACCT CCGTTAATTG  60
 61 ATGTCAACTG GCATCAATTT GAGATACTTT GGGTCAATTT GCAGTGTGCA TTCGCATTCT 120
121 TTGTGTTAAA ATCCTTTTCC CCAGAAGTCG GAGTTTACAG GACACAGGGT GTGGAGCAAT 180
181 TGGGAGAGCT CCAGCAGGGC TGGAGCTCTG CCTCTGCCTC TGCCCCAGGT CCAGGTCCAA 240
241 GTCCAAGTCC AGGTCCAGCG AGAACCGGAG TGAGAGGTGT GTGCTGTGCC TTCCACTAAA 300
301 CGAACCAGTA TCCCAGGTCT CTTAAGTTTC CCAAATCTCG GCATGGTCAG GCCTCTCCAC 360
361 TGTAGCAGCC GCAGCACATT TTTTTTTTTT TTCTCTCTTC TAATGGATCA AGCATCACTA 420
421 CTTATCACAA TTTATCACTT TTTCCAATGA TGTTGCCATT GCCCTTGTTG GCCTTCTCGA 480
481 ACTAGTCCGT CTTTCTGGTT TAACTTGGTG AGGGAAATTC TTAGCACTGG ACTGCGCTGT 540
541 GATATGACCT GTTAAATTAT AACAAGGAGT CGTTTTTCAA TTGACAATTT CTTATCATTG 600
601 TCTCTGGGAT CAATTGGTTT TTCTTCCTCT CTTTCGCTTT TCTCCCCCAC CAACAACACA 660
661 aagctt                                                           666
      |  10       |  20       |  30       |  40       |  50       |  60
```

FIG. 3

YEAST PROMOTER AND ITS USE

The present invention relates to the field of molecular biology. More especially, it relates to a novel DNA sequence possessing transcription promoter activity, to expression vectors containing this sequence and to its use for the production of recombinant proteins, e.g. heterologous proteins. The invention also relates to the recombinant cells containing this DNA sequence.

The progress made in the field of molecular biology has enabled microorganisms to be modified in order to make them produce heterologous proteins. In particular, a large number of genetic studies have focused on the *E. coli* bacterium. However, the industrial application of these novel production methods is still limited, especially by problems of efficacy of expression of the genes in these recombinant microorganisms. Thus, with the aim of increasing the performance of these production systems, research has been performed in order to isolate strong promoters, enabling high levels of expression of heterologous proteins to be obtained. In *E. coli*, the promoters of the tryptophan and lactose operons may be mentioned in particular.

More recently, in *S. cerevisiae* yeast, studies have focused on promoters derived from genes involved in glycolysis. Examples include promoters from the 3-phosphoglycerate kinase PGK gene (Dobson et al., Nucleic Acid Res. 10, 1982, 2625; Hitzeman et al., Nucleic Acid Research 1982, 7791), the glyceraldehyde-3-phosphate dehydrogenase GAPDH gene (Holland et al., J. Biol. Chem. 254, 1979, 9839; Musti et al., Gene 25, 1983, 133), the alcohol dehydrogenase 1 ADH1 gene (Bennentzen et al., J. Biol. Chem. 257, 1982, 3018; Denis et al., J. Biol. Chem. 25, 1983, 1165), and the enolase 1 ENO1 gene (Uemura et al., Gene 45, 1986, 65).

Recently, genetic tools have been developed in order to make use of Kluvveromyces yeast as a host cell for the production of recombinant proteins. The demonstration of a 2-micron type plasmid originating from *K. drosoohilarum* (plasmid pKD1-EP 241,435) has enabled a very effective host/vector system for the production of recombinant proteins to be established (EP 361,991). However, the promoters used in this system have never been optimised. In particular, the promoters in question are essentially heterologous ones, i.e. originating from other microorganisms such as, notably, *S. cerevisiae*. This situation may lead to various disadvantages. The activity of the promoter may be limited because of the absence of certain elements of the transcription machinery (e.g. transactivators). A certain toxicity to the host cell may occur due to an absence of regulation, or the stability of the vector may be affected.

The lack of strong homologous promoters in Kluyveromyces constitutes a limiting factor in the industrial exploitation of this expression system.

The Applicant has now identified, cloned and sequenced a region of the *Kluvveromyces lactis* genome possessing transcription promoter activity (see FIG. 1). More specifically, this region corresponds to the promoter of the *K. lactis* ADH4 gene (K1ADH4) coding for alcohol dehydrogenase IV. This region, or derivatives or fragments thereof, may be used very efficaceously for the production of recombinant proteins in yeasts of the genus Kluyveromvces. This sequence may also be used in other host organisms.

Moreover, analysis of the region of the Kluvveromvces genome obtained has enabled a bidirectional promoter activity to be demonstrated. The complementary strand of the region presented in FIG. 1 also possesses promoter activity acting in the other direction.

Furthermore, another advantage of the promoter activity obtained lies in its regulable character. Depending on the conditions of use (medium, strain), it is possible to control the activity of the promoter and hence to trigger or repress the expression of a recombinant gene.

Another advantage of the promoter region obtained lies in the absence of repression by glucose. This result is surprising, since it represents the first example of a promoter derived from an ADH gene induced by ethanol and not repressed by glucose. In *S. cerevisiae*, the ADH2 gene is expressed on various non-fermentable carbon sources (glycerol, ethanol, lactate, pyruvate) but, in contrast to K1ADH4, the expression of this gene is very strongly repressed when glucose is added to the medium (Denis et al., J.Mol. Biol. 148 (1981) 355). Similarly, expression of the alcA gene which codes for an alcohol dehydrogenase I in *Aspergillus nidulans* is induced by ethanol, but sensitive to repression by glucose (Falenbok, J. Biotechnol. 17 (1991) 11).

A subject of the present invention hence lies in a DNA sequence comprising all or part of the sequence presented in FIG. 1 (SEQ ID NO: 1) or of its complementary strand, or of a derivative of these sequences, and possessing transcription promoter activity.

The term "derivative" is understood to mean any sequence obtained from the sequence given in FIG. 1 (SEQ ID NO: 1) by structural modifications (mutations, deletions, substitutions, additions, fragmentations, etc.) and which retains promoter activity. In particular, the mutations can involve one or more nucleotides, and the additions and/or substitutions can involve regulatory elements or activator regions such as the "UAS" regions.

When a derivative is produced, its transcription promoter activity may be demonstrated in several ways, including, but not limited to, placing a resistance gene or a complementation marker under the control of the sequence under study. Any other technique known to those skilled in the art may also be used for this purpose.

Examples of derivatives according to the invention include, but are not limited to, a promoter comprising the approximately 500-bp SacI-BamHI fragment the sequence of which is presented in FIG. 2 (SEQ ID NO: 2) or an approximately 700-bp SalI-HindIII fragment the sequence of which is presented in FIG. 3 (SEQ ID NO: 3), or the approximately 700-bp BglII-SacI fragment corresponding to the fragment bounded by nucleotides 1 and 723 of the strand complementary to the sequence presented in FIG. 1.

The construction of these promoters is described in detail in the examples.

The sequence presented in FIG. 1 was obtained from an approximately 8-kb BamHI fragment obtained by screening a library of total genomic DNA of *Kluyveromvces lactis* by means of a heterologous probe originating from the *S. cerevisiae* ADH2 structural gene. Applicants have, therefore, shown that it is possible to clone a promoter region in Kluyveromvces by hybridisation using heterologous probes corresponding to an *S. cerevisiae* gene. The details of the cloning of the sequence are given in the examples. The derivatives according to the invention may then be prepared from these sequences, as described in the examples.

Another subject of the invention relates to a recombinant DNA comprising a DNA sequence as defined above.

This recombinant DNA can contain, e.g., the promoter sequence presented in FIG. 1 (SEQ ID NO: 1) or a derivative thereof, into which a restriction site is inserted, facilitating the use of this sequence as a "portable" promoter.

Preferably, this recombinant DNA contains, in addition, one or more structural genes. Examples of such structural genes include, but are not limited to, enzymes (such as, in particular, superoxide dismutase, catalase, amylases, lipases, amidases, chymosin, and the like), blood derivatives (such as serum albumin, alpha- or beta-globin, factor VIII, factor IX, yon Willebrand's factor, fibronectin, $alpha_1$-antitrypsin, and the like), insulin and its variants, lymphokines (such as interleukins, interferons, colony stimulating factors [G-CSF, GM-CSF, M-CSF, etc.], TNF, TRF, and the like), growth factors (such as growth hormone, erythropoietin, FGF, EGF, PDGF, TGF, and the like), apolipoproteins, antigenic polypeptides for the production of vaccines (hepatitis, cytomegalovirus, Epstein-Barr, herpes, and the like), or alternatively fusions of polypeptides such as, in particular, fusions containing an active portion fused to a stabilising portion (e.g. fusions between albumin or albumin fragments and a virus receptor or portion of a virus receptor [CD4,and the like]).

Still more preferably, the recombinant DNA also contains signals enabling the expression product of the said structural gene or genes to be secreted. These signals can correspond to the natural secretion signals of the protein in question, but they can also be of different origin. In particular, secretion signals derived from yeast genes may be used, such as those of the killer toxin (Stark and Boyd, EMBO J. 5 (1986) 1995) or alpha pheromone (Kurjan and Herskowitz, Cell 30 (1982) 933: Brake et al., Yeast 4 (1988) S436) genes.

In a particular embodiment of the invention, the recombinant DNA forms part of an expression plasmid, which can be autonomously replicating or integrative.

In particular, autonomously replicating vectors may be obtained using sequences which replicate autonomously in the chosen host. In particular, in yeast, these can be origins of replication derived from plasmids (pKD1, 2μ, and the like) or alternatively chromosomal sequences (e.g., ARS).

The integrative vectors may be obtained using sequences homologous to certain regions of the host genome, and permit integration of the vector by homologous recombination.

Another subject of the invention relates to the recombinant cells containing a DNA sequence as defined above.

Advantageously, the cells are chosen from yeasts, and still more preferably from yeasts of the genus Kluyveromvces. It is understood, however, that the invention covers all recombinant cells in which the promoter regions of the invention are active.

These cells may be obtained by any method enabling a foreign DNA to be introduced into a cell. Such methods include transformation, electroporation, or any other technique known to those skilled in the art.

Another subject of the invention relates to the use of a sequence as defined above for the expression of recombinant genes.

As illustrated in the examples, the DNA sequences according to the invention permit high levels of production of recombinant proteins.

Moreover, the bidirectional promoter activity of the sequences of the invention makes possible an especially advantageous use. It is possible to use these sequences for the simultaneous expression of several recombinant genes in the two opposite orientations.

Advantageously, the invention relates to the use of a sequence as defined above for the simultaneous expression of two recombinant genes, inserted on each side of the promoter, in the two opposite orientations.

Advantageously, the sequences of the invention may be used for the expression of genes coding for proteins of pharmaceutical or agri-foodstuffs interest. As examples of such proteins, the proteins listed above may be mentioned.

The present invention also makes it possible to carry out a method for the production of recombinant proteins, in which a recombinant cell as defined above is cultured and the protein produced is recovered. As examples of recombinant proteins, the proteins listed above may be mentioned.

Preferably, the method of the invention is applicable to the production of human serum albumin or one of its molecular variants. Molecular variants of albumin is understood to mean the natural variants resulting from the polymorphism of albumin, truncated forms or any hybrid protein based on albumin.

Moreover, an especially advantageous aspect of the invention lies in the possibility of regulating the activity of the promoters. The Applicants have shown that the promoter activity is specifically induced by ethanol. The inducer ethanol may either be added directly to the culture medium, or may be produced intracellularly by the host cell, according to its capacities for fermentation, from the carbon source introduced into the medium. Regulation may hence be obtained under several conditions:

- either by culturing the recombinant cell in a medium containing a carbon source which is different from ethanol and cannot be converted to ethanol by the cell. In this case, the activity of the promoter is induced by adding ethanol to the medium. For example, in the case of *K. lactis* 2359/152 and *K. lactis* MW98-8C, the KiDH4 promoter is inactive when the cells are cultured on a medium containing glycerol, but is induced after adding ethanol.
- or by culturing, in a medium containing a fermentable carbon source (e.g. glucose), a recombinant cell possessing a deficiency in respect of its fermentative metabolism and, as a result, incapable of producing ethanol from this carbon source. In this case, the activity of the promoter is induced either by adding ethanol to the medium, or by adding another fermentable sugar participating in a step. downstream of the deficient step and capable of being metabolised to ethanol in spite of the said deficiency. By way of example, a strain possessing a rag2 mutation, and as a result not possessing phosphoglucose isomerase activity, may be used. In this case, the K1ADH4 promoter is inactive on glucose medium, and the activity of the promoter may be induced by adding ethanol or fructose.

Other advantages of the present invention will become apparent on reading the examples which follow, which are to be considered as illustrative and non-limiting.

LEGEND TO THE FIGURES

FIG. 1: Nucleotide sequence (SEQ ID NO: 1) of the 1.2-kb fragment corresponding to the K1ADH4 promoter of *K. lactis*.

FIG. 2: Nucleotide sequence (SEQ ID NO: 2) of the approximately 0.5-kb SacI-BamHI fragment corresponding to the truncated K1ADH4 promoter in the vector pP4-15Kan.

FIG. 3: Nucleotide sequence (SEQ ID NO: 3) of the approximately 0.7-kb SalI-HindIII fragment corresponding to the truncated K1ADH4 promoter in the vectors pYG129 and pYG130.

FIG. 4: Diagrammatic representation of plasmid p6-4-98 and construction of plasmids p6-2200-2 and pP4-33.

Figure 5:
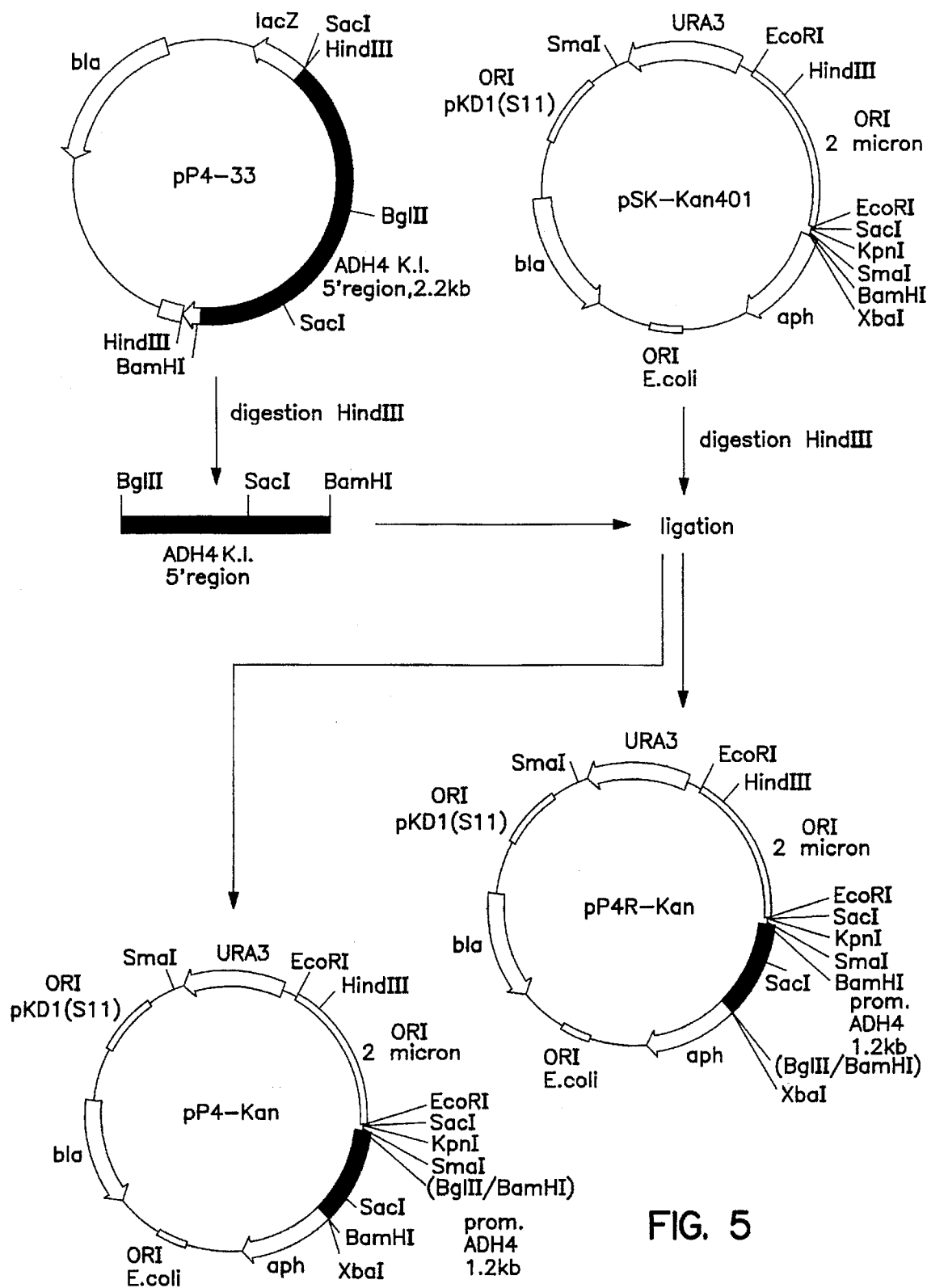

FIG. 5: Diagrammatic representation of plasmid pSK-Kan401 and construction of plasmids pP4-Kan and pP4R-Kan.

Figure 6:
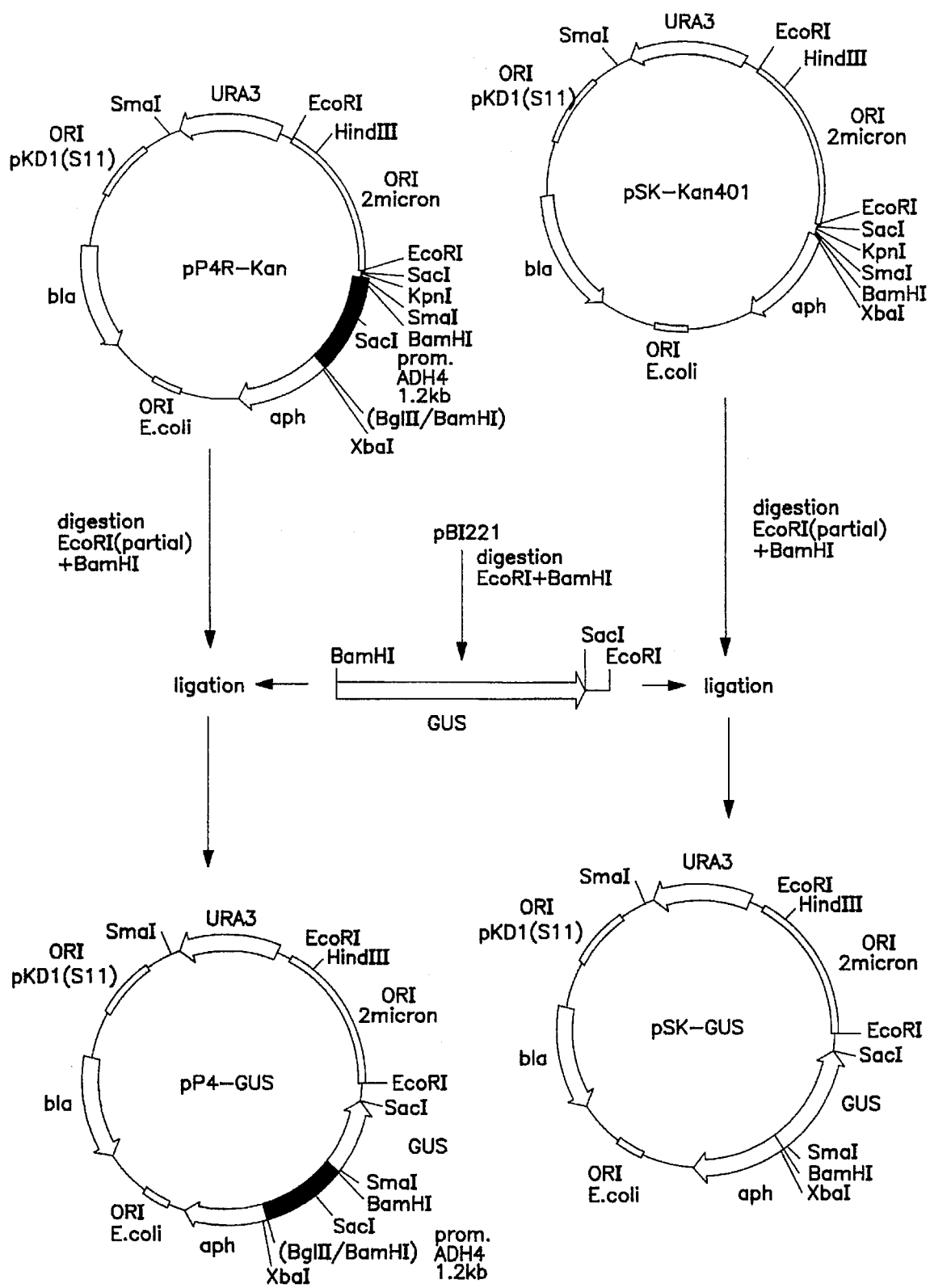

FIG. 6: Construction and representation of plasmids pP4-GUS and DSK-GUS.

Figure 7:
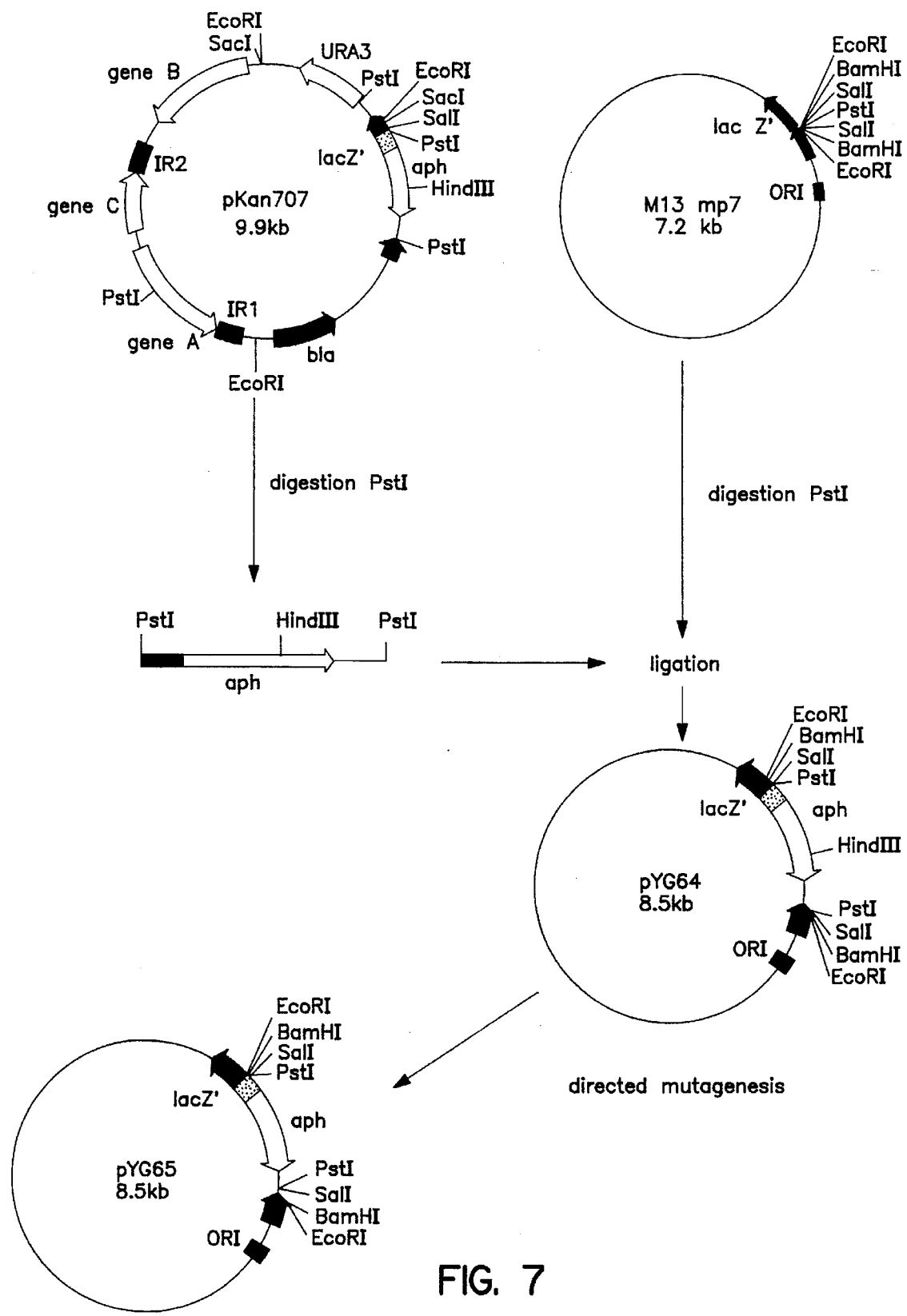

FIG. 7: Diagrammatic representation of plasmid pKan707 and construction of the phage M13 derivatives pYG64 and DYG65.

Figure 8:
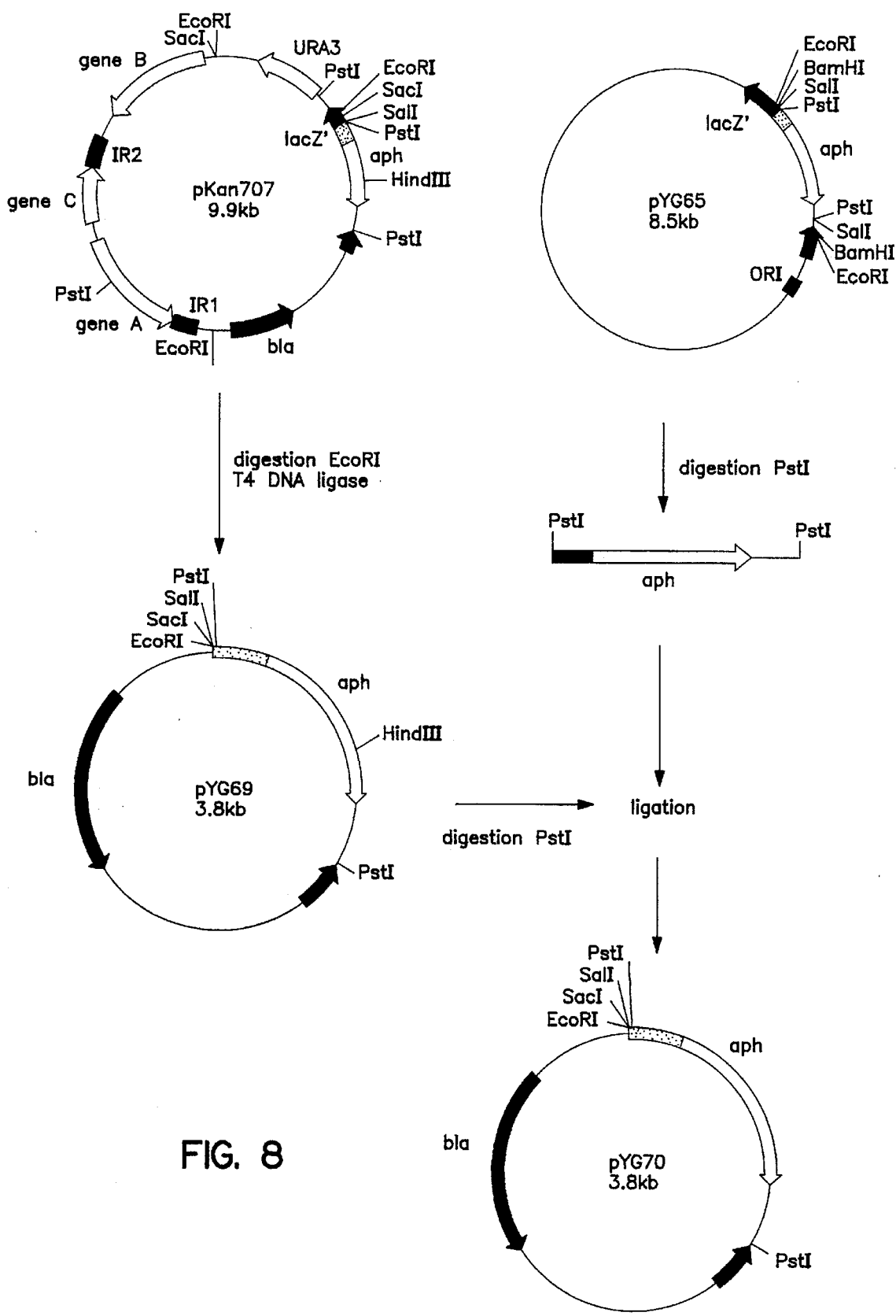

FIG. 8: Construction and representation of plasmids pYG69 and pYG70.

Figure 9:
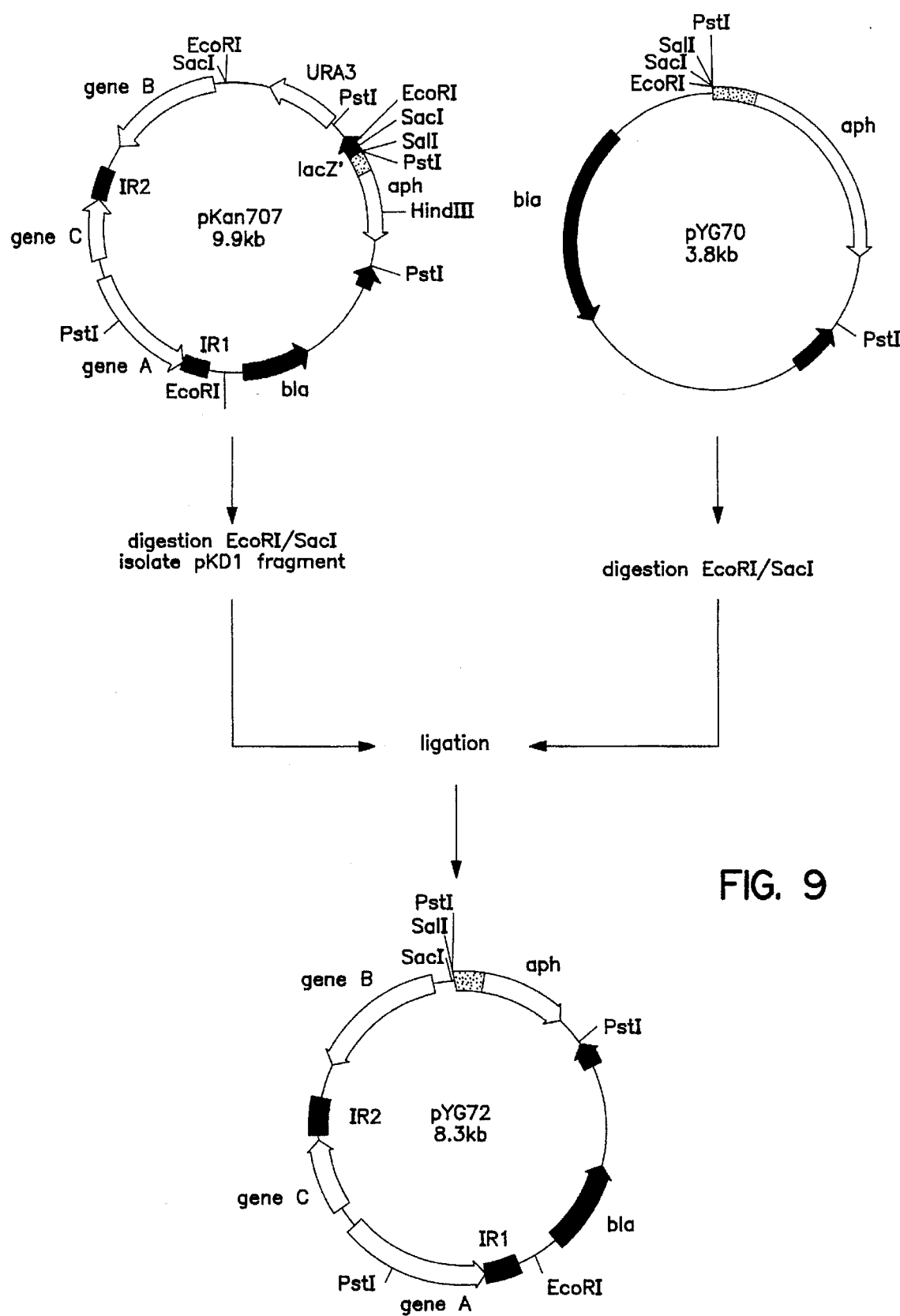

FIG. 9: Construction and representation of plasmid pYG72.

Figure 10:
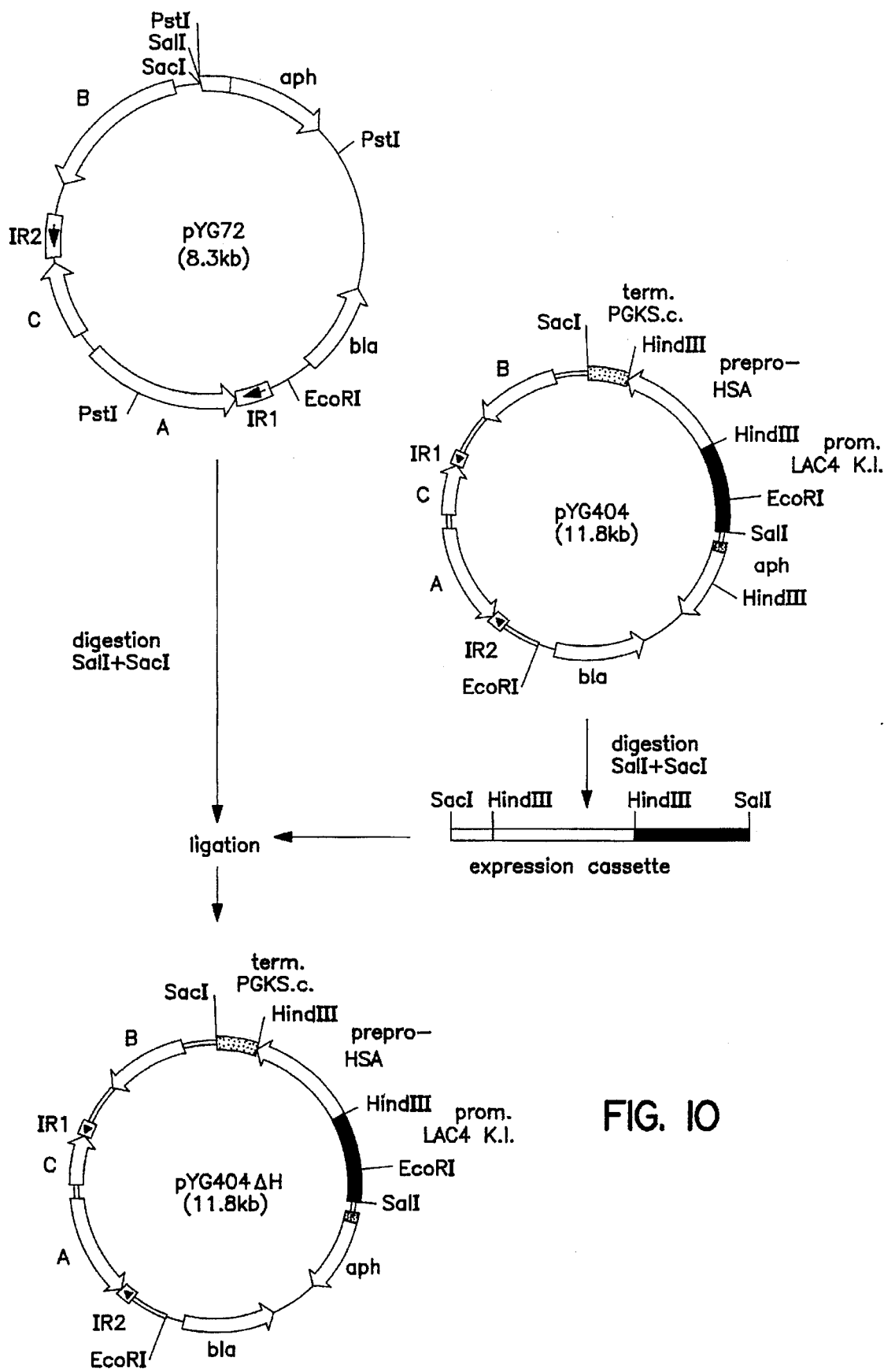

FIG. 10: Diagrammatic representation of plasmid pYG404 and construction of plasmid pYG404AH.

Figure 11:
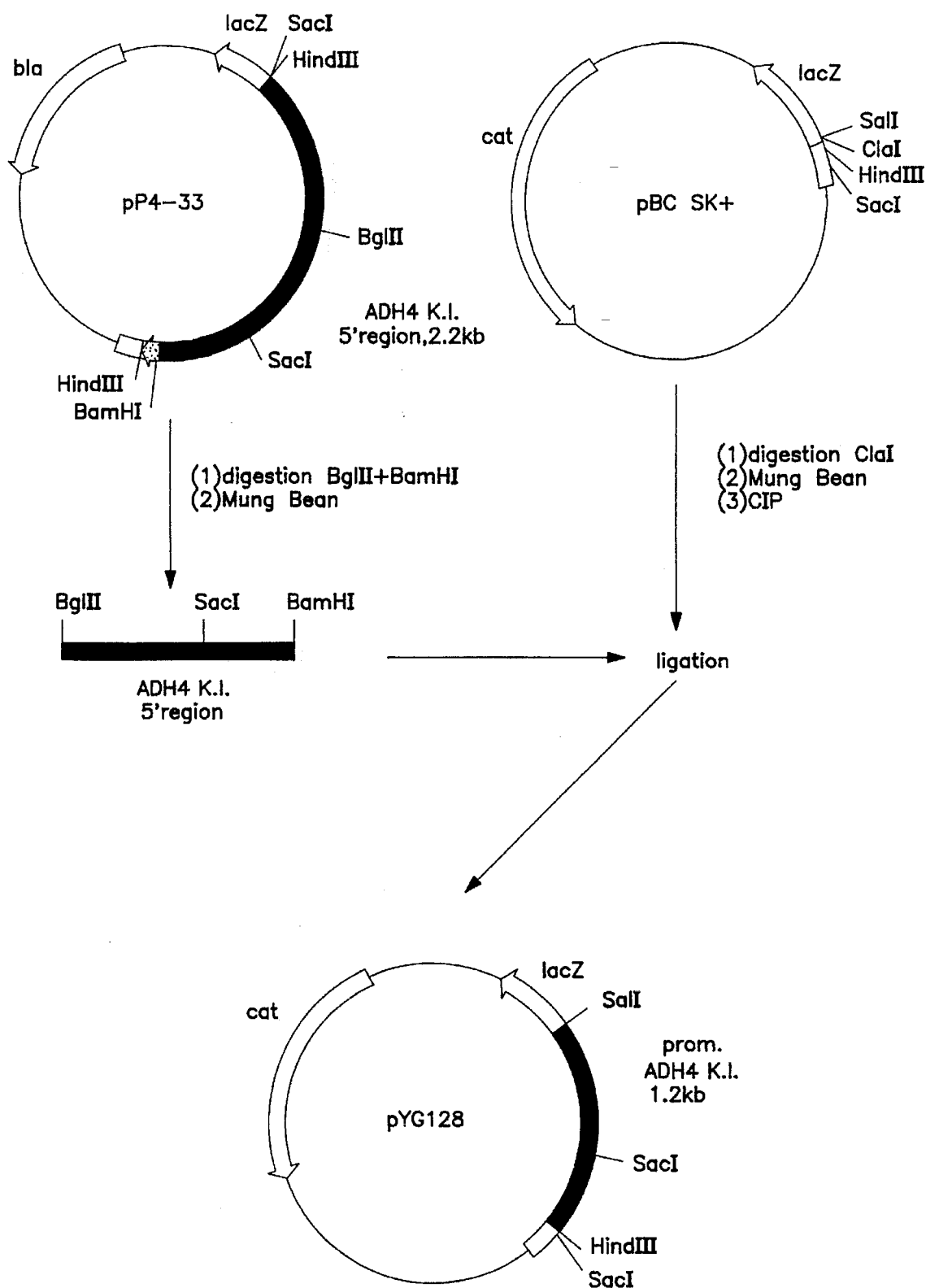

FIG. 11: Construction and representation of plasmid pYG128.

Figure 12:
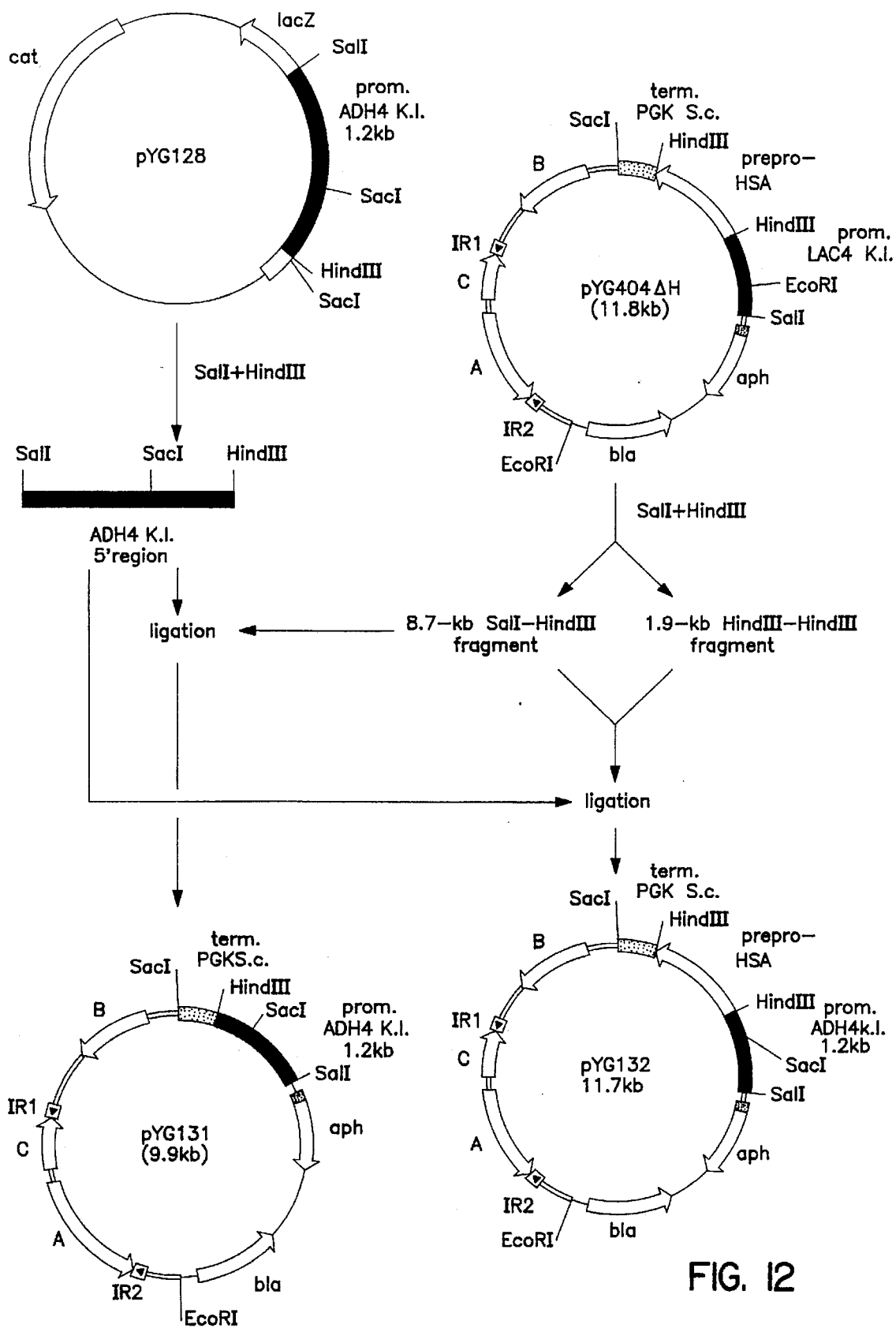

FIG. 12: Construction and representation of plasmids pYG131 and pYG132.

Figure 13:
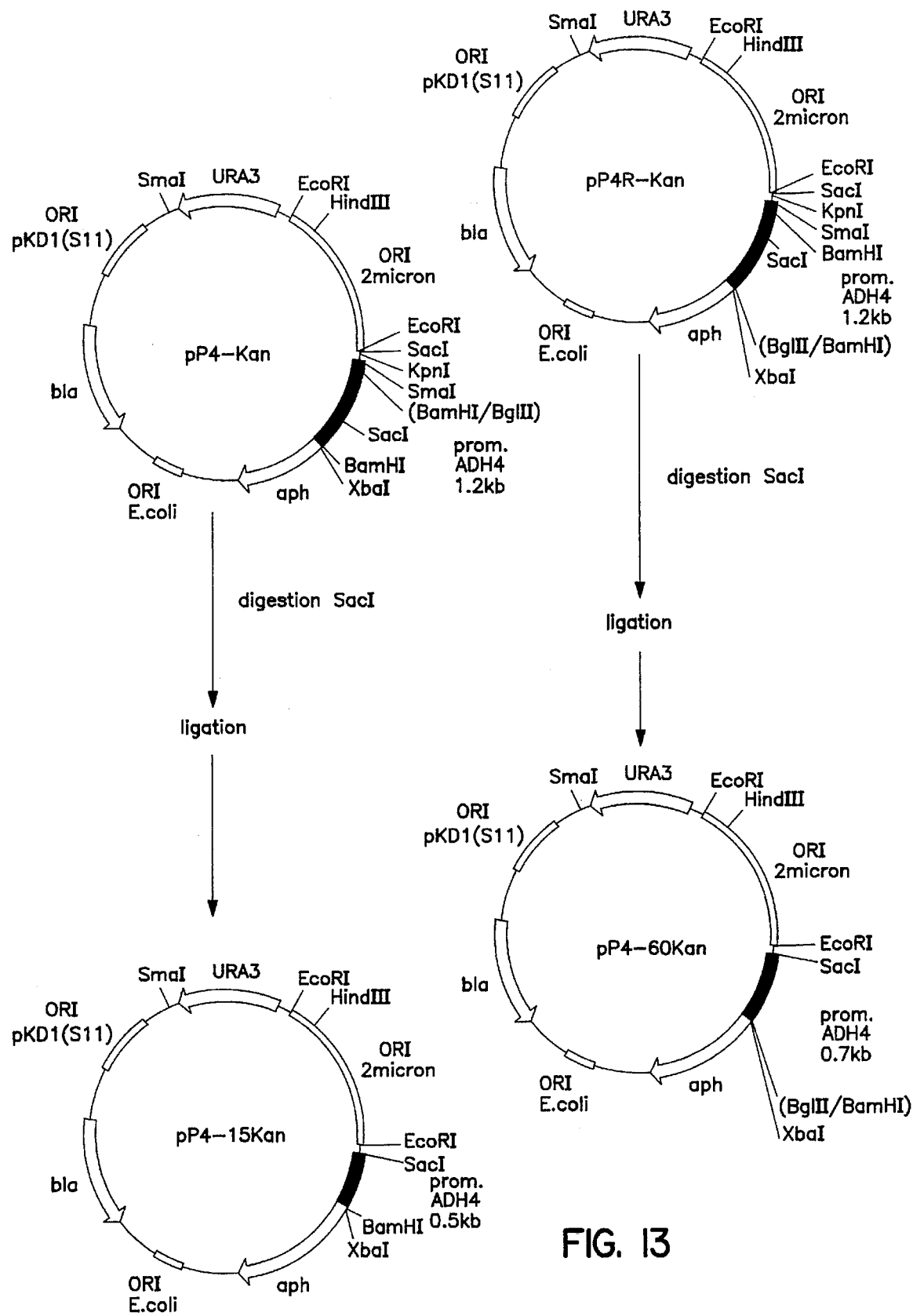

FIG. 13: Construction and representation of plasmids pP4-15Kan and pP4-60Kan.

Figure 14:
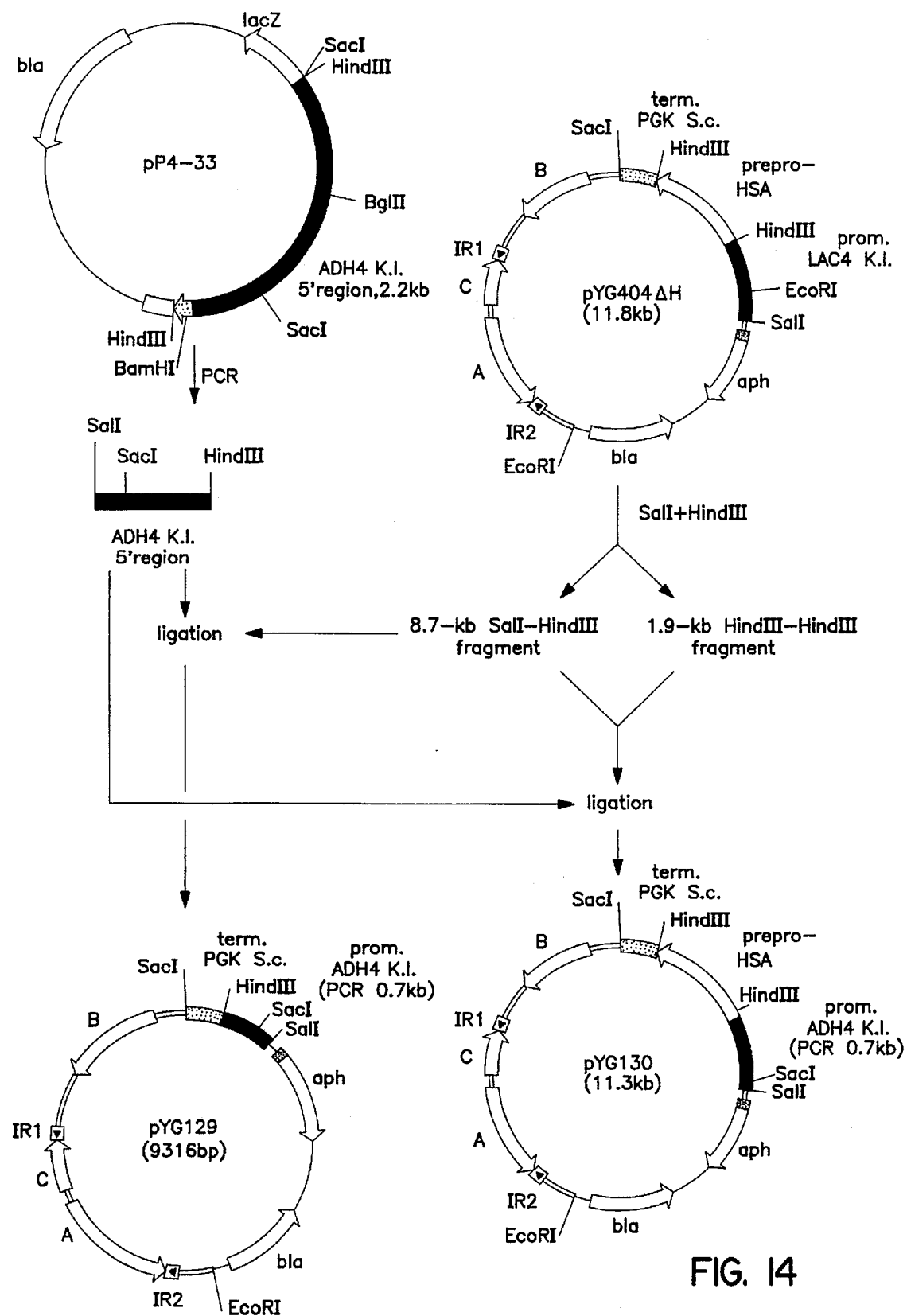

FIG. 14: Construction and representation of plasmids pYG129 and pYG130.

Figure 15:
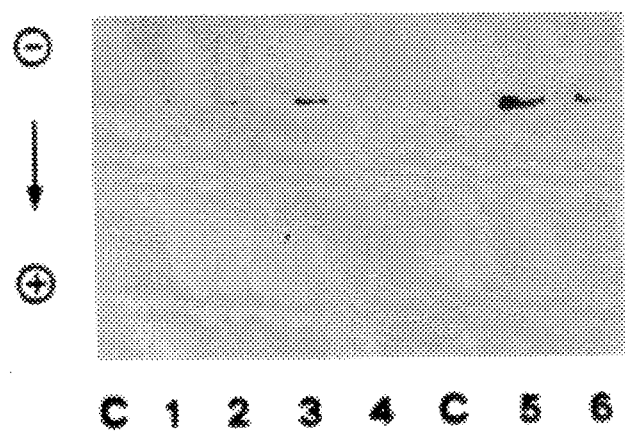

FIG. 15: Native polyacrylamide gel (5%) stained according to the protocol described in Example 7.1.2, demonstrating the expression of β-glucuronidase activity in the strain MW98-8C transformed with plasmid pP4-GUS (lanes 1-6 correspond to 6 independent clones). The results obtained from the strain MW98-8C transformed with plasmid pSK-GUS (control) are shown in lanes C.

Figure 16:
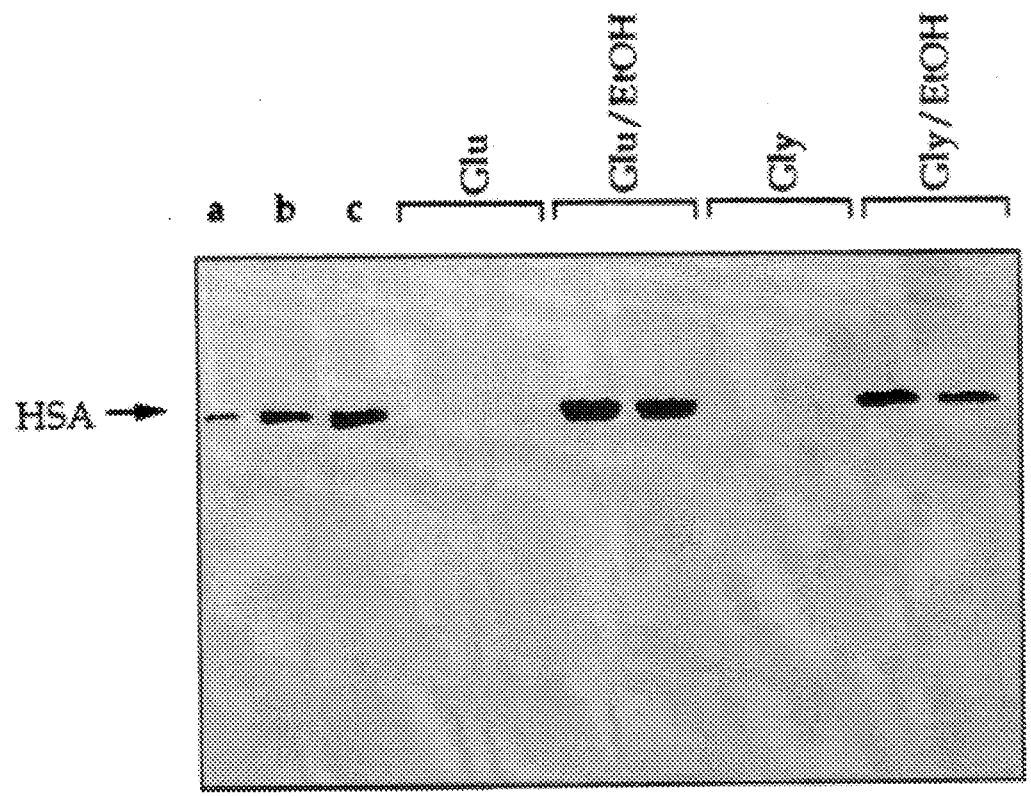

FIG. 16: 8.5% SDS-polyacrylamide gel stained with Coomassie blue, demonstrating the secretion of human serum albumin from the strain MW98-8C transformed with the vector pYG132. Lanes a–c, albumin extracted from human plasma (Sigma) used as a standard and spotted at increasing concentrations (0.5, 1.0 and 1.5 μg per lane). The other lanes correspond to 25 μl of culture supernatant obtained from the media described in Example 7.2.1. Glu, glucose; Glu/EtOH, glucose/ethanol; Gly, glycerol; Gly/EtOH, glycerol/ethanol.

Figure 17:
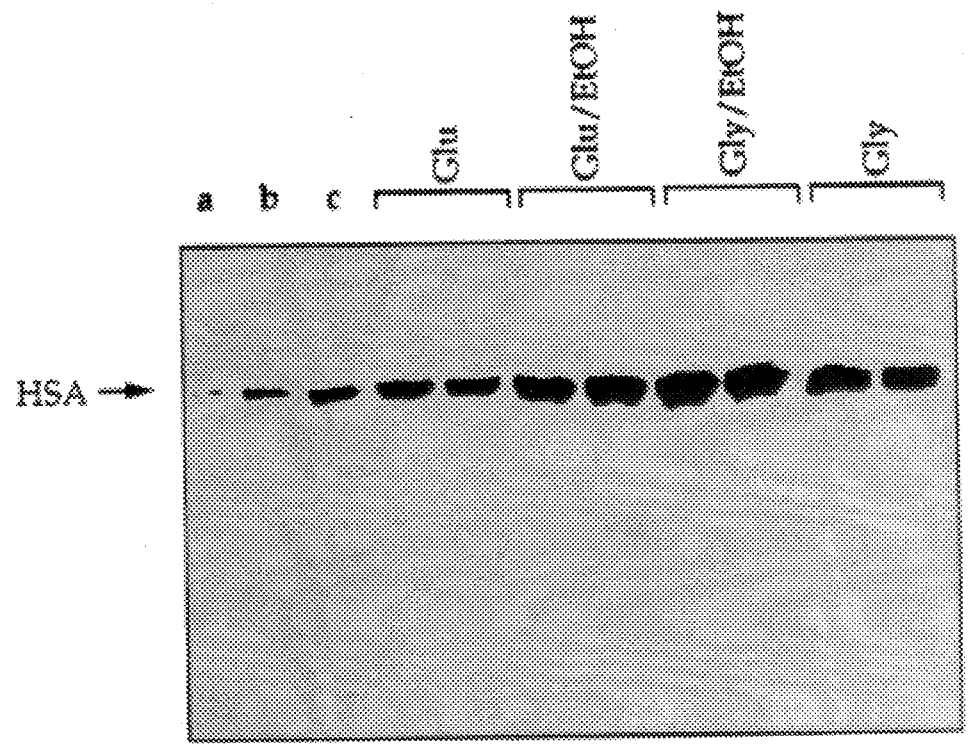

FIG. 17: 8.5% SDS-polyacrylamide gel stained with Coomassie blue, demonstrating the secretion of human serum albumin from the strain CBS 293.91 transformed with the vector pYG132. Lanes a–c, albumin extracted from human plasma (Sigma) used as a standard and spotted at increasing concentrations (0.5, 1.0 and 1.5 g per lane). The other lanes correspond to 25 μl of culture supernatant obtained from the media described in Example 7.2.1. Glu, glucose; Glu/EtOH, glucose/ethanol; Gly, glycerol; Gly/EtOH, glycerol/ethanol.

Figure 18:
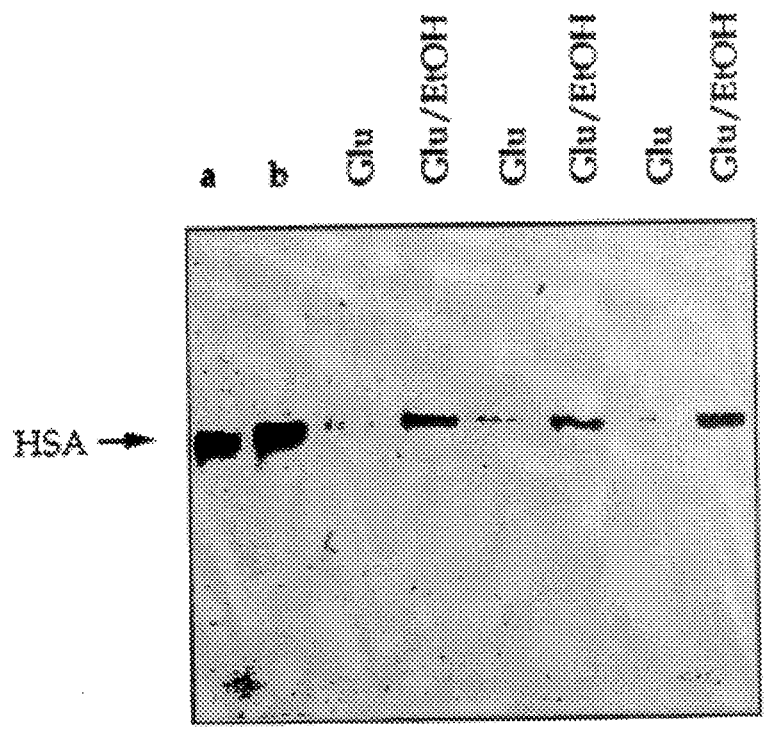

FIG. 18: 8.5% SDS-polyacrylamide gel stained with Coomassie blue, demonstrating the secretion of human serum albumin from the strain CBS 293.91 transformed with the vector pYG130. Lanes a–b, albumin extracted from human plasma (Sigma) used as a standard and spotted at increasing concentrations (0.5 and 1.0 μg per lane). The other lanes correspond to 25 μl of culture supernatant obtained from the media described in Example 7.2.1. Glu, glucose; Glu/EtOH, glucose/ethanol.

Table 1: Summary of the various constructions performed using the whole KiDH4 promoter (1.2-kb fragment, either in the form of a BglII-BamHI fragment [pP4-Kan, pP4R-Kan and pP4-GUS], or in the form of a SalI-HindIII fragment [pYG131 and pYG132]).

Table 2: Summary of the various constructions performed using the truncated K1ADH4promoter (0.5-kb SacI-BamHI fragment the nucleotide sequence of which is given in FIG. 2 [pP4-15Kan]; 0.7-kb BglII-SacI fragment corresponding to positions 1–723 of the nucleotide sequence given in FIG. 1 [pP4-60Kan]; 0.67-kb SalI-HindIII fragment the nucleotide sequence of which is given in FIG. 3 [pYG129 and pYG130]).

Table 3: Study of regulation of the expression of the K1ADH4 gene. The presence or absence of ADH IV enzymatic activity demonstrated according to the protocol described in Example 5 is indicated by the symbols + or –.

GENERAL CLONING TECHNIQUES

The standard methods of molecular biology such as caesium chloride/ethidiumbromide gradient centrifugation of plasmid DNA, digestion with restriction enzymes, gel electrophoresis, electro-elution of DNA fragments from agarose gels, transformation in *E. coli*, and the like, are described in the literature (Maniatis et al., "Molecular Cloning: a Laboratory Manual", Cold Spring Harbor Laboratory, Cold Spring Harbor, N.Y., 1986: Ausubel et al., (eds.), "Current Protocols in Molecular Biology", John Wiley & Sons, New York 1987).

Oligodeoxynucleotide-directed in vitro mutagenesis is performed according to the method described by Taylor et al. (Nucleic Acids Res. 13 (1985) 8749–8764) using the kit distributed by Amersham. Nucleotide sequencing is carried out according to the dideoxy technique described by Sanger et al. (Proc. Natl. Acad. Sci. USA, 74 (1977) 5463–5467). Enzymatic amplification of specific DNA fragments is performed by the PCR reaction (polymerase-catalysed chain reaction) under the conditions described by Mullis and Faloona (Meth. Enzym., 155 (1987) 335–350) and Saiki et al (Science 230 (1985) 1350–1354) using a "DNA thermal cycler" (Perkin Elmer Cetus), following the manufacturer's recommendations.

EXAMPLES

Plasmids and Strains Used in the Examples

The following plasmids were used in the various cloning steps, or in the construction of expression vectors.
Replacement vector Lambda-L47: Loenen and Brammar, Gene Q. (1980) 249–259;
Plasmid pBR322 (Pharmacia, Uppsala, Sweden);
Plasmid pTZ19 (Pharmacia, Uppsala, Sweden);
Plasmid pSK-Kan401: Chen and Fukuhara, Gene 69 (1988) 181–192;
Plasmid pBI221 (Clontech Laboratories, Palo Alto, Calif. USA);
Plasmid pBC SK +/– (Stratagne, La Jolla, Calif. USA);
Plasmid pYG404 (EP 361,991);
Plasmid pKan707 (EP 361,991);
Bacteriophage M13mp7: Messing et al., Proc. Natl. Acad. Sci. USA 74 (1977) 3652.

The following strains were used for the cloning, construction and use of the promoters of the invention.
*K. lactis* CBS2359/152 (No. CBS 289.91)
*K. lactis* MW98-8C (No. CBS 579.88)
*K. lactis* CBS 293.91

Example 1: Isolation of the K1ADH4 of *K. lactis*

The sequence presented in FIG. 1 (SEQ ID NO: 1) obtained by screening a library of total genomic DNA of *Kluvveromyces lactis* CBS2359/152 using a heterologous probe originating from the *S. cerevisiae* ADH2 gene. More specifically, the library was obtained by cloning the product of partial digestion of *K. lactis* CBS2359/152 DNA with the enzyme Sau3A at the BamHI site of the replacement vector Lambda-L47. The probe used for hybridisation was a 980-bp EcoRV-BamHI fragment comprising the coding region of the *S. cerevisiae* ADH2 structural gene with the exception of the first 70 bp (probe A). This fragment was obtained by enzymatic digestion of the plasmid designated pBR322. ADR2. BSa (Williamson et al., Cell 23 (1981) 605-614; Russell et al., J. Biol. Chem. 258 (1983) 2674-2682).

An approximately 8-kb fragment was thereby isolated and was subcloned at the BamHI site of plasmid pBR322 to generate plasmid p6-4-98 (FIG. 4). The BamHI insert carried by this plasmid was then mapped by means of restriction enzymes, and the promoter region of the K1ADH4 gene was localized on this fragment by differential hybridisations using probe A as well as a second probe corresponding to the approximately 1100-bp BamHI-EcoRV fragment of plasmid pBR322. ADR2. BSa (probe B).

In a second step, plasmid p6-4-98 was digested with the enzyme HindIII and a 2.2-kb fragment was isolated. This fragment was purified by standard techniques and subcloned at the HindIII site of plasmid pTZ19 to generate plasmid p6-2200-2 (FIG. 4). Analysis of the subcloned fragment revealed that it contains the first 14 codons of the K1ADH4 gene and the region located upstream, comprising the elements which regulate expression.

The portion bounded by the BglII site and the ATG translation initiation codon (approximately 1.2-kb fragment) was sequenced using the chain termination method (Sanger et al., Proc. Nat. Acad. Sci. 74 (1977) 5463). The sequence of this fragment is presented in FIG. 1 (SEQ ID NO: 1).

Example 2: Construction of a Portable K1ADH4 Promoter BglII-BamHI)

A portable promoter was prepared by inserting a BamHI restriction site at position −16 (relative to the ATG codon) of the K1ADH4 gene into the 2.2-kb HindIII fragment present in plasmid p6-2200-2.

The insertion of this site enabled a 1.2-kb BglII-BamHI fragment exclusively comprising the K1ADH4 promoter region to be generated. It also enabled any gene which it is desired to express to be introduced downstream of the promoter thereby obtained.

The BamHI site was introduced at position −16 (relative to the translation initiation site (ATG)) of the K1ADH4 gene by directed mutagenesis using the double primer technique (Sambrook, Fritsch, Maniatis, Molecular Cloning Laboratory Manual, Cold Spring Harbor Lab Press, 1989). The sequence of the synthetic oligo-deoxynucleotides used for this mutagenesis is given below. The BamHI site generated is underlined, the ATG is shown in italics and the asterisks denote the bases modified relative to the initial sequence. IS=Initial sequence; MS=Modified sequence.

| | |
|---|---|
| 5'-CTCCCCCACCAACAACACAACATACAACACACGCAA*TG*TTCAGATT-3'(IS) <br>                                        ** * | (SEQ ID NO: 4) |
| 5'-CTCCCCCACCAACAACAC<u>AGGATCC</u>AACACACGCAA*TG*TTCAGATT-3'(MS) | (SEQ ID NO: 5) |
| 3'-GAGGGGGTGGTTGTTGTGTCCTAGGTTGTGTGCGTTACAAGTCTAA-5'(MS) | (SEQ ID NO: 6) |

The plasmid thereby obtained is referred to as pP4-33 (FIG. 4).

Example 3: Construction of Cloning or Expression Vectors Containing the Whole Promoter Table 1 collates the constructions described in this example.

3.1. Construction of a Vector for Expression of the aph Gene:

The DNA of plasmid pP4-33 (see Example 2) was digested with BglII and BamHI to generate a 1.2-kb fragment containing the K1ADH4 promoter. This fragment was then introduced at the BarnHi site of plasmid pSK-Kan401, upstream of the aDh reporter gene coding for aminoglycoside 3'-phosphotransferase (I) (Oka et al., J. Mol. Biol. 147 (1981) 217) lacking its own promoter, which, when expressed, confers geneticin (G418) resistance on the yeast (Jimenez and Davies, ref). After amplification in *E.coli*, 2 recombinant plasmids were obtained, differing in the orientation of the insert. In plasmid pP4-Kan, the 1.2-kb fragment is in the same orientation relative to the aph gene as that observed in the ADH4 context, whereas it is in the opposite orientation in plasmid pP4R-Kan (see FIG. 5).

3.2. Construction of a Vector for Expression of the GUS and aph Genes:

Plasmid pP4R-Kan was used to construct an expression vector in which 2 heterologous genes lacking their own promoters are placed on the two sides of the 1.2-kb K1ADH4 promoter. The heterologous genes used were:

- the aph gene, expression of which confers G418 resistance, and
- the *E. coli* β-glucuronidase gene (GUS gene), expression of which may be demonstrated by an enzymatic reaction.

To carry out this construction, plasmid pP4R-Kan was digested with EcoRI and BamHI. Separately, the *E. coli* β-glucuronidase gene was isolated from plasmid pBI221 in the form of a 2.1-kb BamHI-EcoRI fragment. The latter was then introduced by ligation into plasmid pP4R-Kan linearised as described, to generate plasmid pP4-GUS (see FIG. 6). In parallel, a control plasmid was prepared by inserting the 2.1-kb BamHI-EcoRI fragment derived from plasmid pBI221 carrying the GUS gene into plasmid pSK-Kan401 digested beforehand with BamHI and EcoRI. The plasmid thereby obtained is referred to as pSK-GUS (FIG. 6). This construction differs from plasmid pP4-GUS only by the absence of the 1.2-kb K1ADH4 promoter.

3.3. Construction of a Vector for Expression of the Gene Coding for Human Serum Albumin (HSA):

To construct various vectors for expression of human serum albumin, a derivative of plasmid pYG404 (see EP 361,991) was prepared, containing:

- a yeast replicon (virtually the whole sequence of the natural plasmid pKD1),
- the gene coding for human preproalbumin (HSA) under the control of the *K. lactis* LAC4 gene and followed by the *S. cerevisiae* PGK gene terminator; the structural gene coding for HSA is preceded by a sequence of 25 nucleotides corresponding to the region directly upstream of the *S. cerevisiae* PK gene, the aph gene conferring geneticin (G418) resistance on the yeast, and a replicon and a selectable marker (bla gene conferring ampicillin resistance) for *E. coli*.

This plasmid, designated pYG404ΔH, differs from pYG404 only by the destruction of the HindIII site, localised in the aph gene, by directed mutagenesis. This modification then enabled the LAC4 promoter present in plasmid pYG404ΔH in the form of a SalI-HindIII fragment to be replaced by different variants of the K1ADH4 promoter, also constructed as portable promoters in the form of SalI-HindIII fragments.

3.3.1. Construction of Plasmid pYG404ΔH (FIGS. 7–10):

To accomplish the deletion of the HindIII site in the cloning vector pYG404, various steps of subcloning were performed, giving rise to an intermediate construction: pYG72 (FIG. 9). This vector corresponds to plasmid pKan707 (EP 361,991) in which the SacI fragment containing the URA3 gene has been removed, together with the single HindIII site present in the aph gene. To perform directed mutagenesis on this site, the 1.3-kb PstI fragment carrying the aph gene was subcloned from plasmid pKan707 into bacteriophage M13mp7 to give the vector pYG64 (FIG. 7). The HindIII site was destroyed by directed mutagenesis (see general cloning techniques) using the following oligodeoxynucleotide: 5'-GAA ATG CAT AAG CT TTG CCA TTC TCA CCG-3' (SEQ ID NO: 7), permitting replacement of the triplet CTT coding for leucine 185 by the triplet CTC. This change does not modify the resulting protein sequence. The plasmid obtained was referred to as pYG65 (FIG. 7). To construct plasmid pYG72, the portion containing the bacterial replicon of the vector pKan707 was isolated by digestion with the enzyme EcoRI and recircularisation with T4 DNA ligase, generating the intermediate plasmid pYG69. The PstI fragment present in the latter, containing the aph gene, was then replaced by the mutated equivalent fragment originating from plasmid DYG65. This construction was referred to as pYG70 (FIG. 8). The 4.7-kb sequence of DKD1 bounded by the EcoRI and SacI sites was then introduced into this vector to obtain pYG72 (FIG. 9).

The vector pYG404ΔH was obtained by inserting the expression cassette originating from plasmid pYG404 (EP 361,991) in the form of a SalI-SacI fragment at the corresponding sites of pYG72 (FIG. 10).

3.3.2. Construction of a Portable K1ADH4 promoter [SalI-HindIII] (FIG. 11):

The klADH4 promoter carried on the BglII-BamHI fragment originating from plasmid pP4-33 (Example 2) was modified in the following manner to adapt it for use in expression vectors derived from plasmid pYG404ΔH:

After digestion of plasmid pP4-33 with the enzymes BglII and BamHI, followed by treatment with mung bean nuclease to make the ends blunt, the 1.2-kb fragment carrying the K1ADH4 promoter was isolated from an agarose gel and subcloned into the vector pBC SK+(Stratagene, La Jolla, Calif., USA) linearised beforehand with the enzyme ClaI and treated with mung bean nuclease as well as with calf alkaline phosphatase (CIP). The plasmid obtained in this manner (pYG128, FIG. 11) enables the K1ADH4 promoter to be isolated in the form of a 1.2-kb SalI-HindIII fragment.

3.3.3. Construction of the Vectors pYG131 and pYG132 (FIG. 12):

Digestion of the expression vector pYG404ΔH (Example 3.3.1) with the enzymes SalI and HindIII enables the LAC4 promoter to be replaced by the K1ADH4 promoter described above.

To perform this cloning, the 8.7-kb SalI-HindIII fragment, containing the pKD1 portion and the selectable markers, and also the 1.9-kb HindIII-HindIII fragment carrying the gene coding for prepro-HSA were isolated from the vector pYG404ΔH, and religated in the presence of a 1.2-kb SalI-HindIII fragment originating from plasmid pYG128 and carrying the K1ADH4 promoter. Two plasmids were obtained in this manner:

pYG131 (FIG. 12), corresponding to a cloning vector enabling any gene which is desirable to express to be inserted at the single HindIII site under the control of the K1ADH4 promoter, and pYG132 (FIG. 12), which is identical to plasmid pYG131 except that it contains the prepro-HSA gene introduced at the HindIII site.

Example 4: Construction of Cloning or Expression Vectors Containing Truncated Derivatives of the K1ADH4 Promoter Table 2 collates the constructions described in this example.

4.1. Construction of Vectors for Expression of the aph Gene:

Plasmids pP4-Kan and pP4R-Kan (Example 3.1.) were used to prepare constructions containing reduced forms of the promoter. For this purpose, plasmids pP4-Kan and pP4R-Kan were digested with the enzyme SacI and then religated, according to the scheme described in FIG. 13.

This manipulation made it possible:

to excise from plasmid pP4-Kan the approximately 0.7-kb SacI fragment located on the side opposite to the aph gene. In the plasmid obtained (pP4-15Kan), the ph gene is hence under the control of a reduced promoter corresponding to the 0.5-kb SacI-BamHI fragment the sequence of which is given in FIG. 2 (SEQ ID NO: 2), in the same orientation as that observed in the ADH4 context.

to excise from plasmid pP4R-Kan the approximately 0.5-kb SacI fragment located on the side opposite to the aph gene. In the plasmid obtained (pP4-60Kan), the aph gene is hence under the control of a reduced promoter corresponding to the strand complementary to the 0.7-kb BglII-SacI fragment (nucleotides 1 to 723) which forms part of the sequence given in FIG. 1.

4.2. Construction of a vector for expression of the prepro-HSA gene:

4.2.1. Construction of a Portable Truncated K1ADH4 promoter [SalI-HindIII] (FIG. 14)

A truncated derivative of the 1.2-kb BglII-BamHI fragment originating from plasmid pP4-33 and carrying the whole K1ADH4 promoter was obtained by enzymatic amplification (PCR) of a portion of this promoter, located between the BsmAI site at position 541 in the sequence given in FIG. 1 and the BamHI site at position −16 relative to the ATG of the ADH4 gene. The oligodeoxynucleotides used for the PCR reaction were:

5'-GGGGTCGACGCGAGACAACACTATTGTGAG-3' (SEQ ID NO: 8), introducing a SalI site (sequence underlined) immediately upstream of the abovementioned BsmAI site, and 5'-GGGAAGCTTTGTGTTGTTGATGGGGGAG-3' (SEQ ID NO: 9), replacing the BamHI site present in the construction pP4-33 by a HindIII site (sequence underlined).

4.2.2. Construction of the Vectors pYG129 and pYG130

The 672-bp fragment obtained by PCR was digested with the enzymes SalI and HindIII, purified from an agarose gel and ligated with the 8.7-kb SalI-HindIII fragment containing the pKD1 portion and the selectable markers originating from the vector pYG404ΔH. This ligation was performed in the presence of the 1.9-kb HindIII—HindIII fragment carrying the gene coding for prepro-HSA isolated from the same vector. Two plasmids were obtained in this manner:

pYG129 (FIG. 14), corresponding to a cloning vector enabling any gene which it is desirable to express to be inserted at the single HindIII site under the control of the truncated K1ADH4 promoter, and pYG130 (FIG. 14), which is identical to plasmid pYG129 except that it contains the prepro-HSA gene introduced at the HindIII site.

The nucleotide sequence of the approximately 0.7 kb SalI-HindIII fragment (SEQ ID NO: 3) corresponding to the truncated K1ADH4 promoter used in these two constructions is given in FIG. 3.

Example 5: Study of the regulation of the expression of the K1ADH4 gene

This study was carried out with the strains *K. lactis* MW98-8C and *K. lactis* 2359/152.

The strain MW98-8C possesses a Rag2⁻ phenotype due to a mutation (rag2) in the gene coding for phosphoglucose isomerase (PGI), which renders it incapable of producing ethanol on a glucose medium. The strain 2359/152 is Rag2⁺.

The activity of the ADH4 promoter was determined under different culture conditions by measuring ADH IV activity using the technique described by Lutstorf and Megnet (Archiv. Biochem. Biophys. 126 (1968) 933). The results obtained are collated in Table 3.

These results show that the activity of the K1ADH4 promoter is specifically induced by ethanol and not depressed in the absence of glucose. In effect, we found that, surprisingly, in contrast to the promoters of other alcohol dehydrogenases such as *S. cerevisiae* ADH2 or *A. nidulans* alcA, the K1ADH4promoter is not repressed by glucose (Table 3). The inducer ethanol may either be added to the culture medium or be produced intracellularly by fermentation of a carbon source such as glucose or fructose (Table 3).

We also showed that a strain mutated in a gene involved in glycolysis, and for this reason incapable of producing ethanol from glucose, may be advantageously used as a host for the expression vectors of the invention. In effect, the K1ADH4 promoter is inactive in a medium containing glucose as the sole carbon source in strains such as MW98-8C (rag2) in which the gene coding for phosphoglucose isomerase is defective. In this strain, activation of the K1ADH4 promoter is accomplished by adding ethanol to the culture medium.

Moreover, we have found that, surprisingly, in the strains CBS2359/152 and MW98-8C, the K1ADH4 promoter is inactive in a medium containing glycerol as the sole carbon source. This result differs from what is known for the promoter of the *S. cerevisiae* alcohol dehydrogenase II gene (ADH2), which is active on various non-fermentable carbon sources including glycerol.

These results hence show that some strains such as CBS2359/152,even with a Rag⁺ phenotype, can enable a regulated expression of the K1ADH4 promoter to be obtained: cells cultured in the presence of glycerol as the sole carbon source do not produce the protein for which the gene is placed under the control of the K1ADH4 promoter (non-induced promoter), while they can be induced for the production of this protein by adding ethanol to the culture medium.

Example 6: Transformation of Kluyveromyces

Various techniques enabling DNA to be introduced into yeast may be used.

Advantageously, the various Kluvveromyces strains used were transformed by treating whole cells in the presence of lithium acetate and polyethylene glycol according to the technique described by Ito et al. (J. Bacteriol. 153 (1983) 163–168). The transformation technique described by Durrens et al. (Curr. Genet. 18 (1990) 7) using ethylene glycol and dimethyl sulphoxide has also been used. It is also possible to transform yeasts by electroporation, e.g. according to the method described by Karube et al. (FEBS Letters 182 (1985) 90).

An alternative protocol has also been described in detail in Application EP 361,991.

Example 7: Use of Expression Vectors for the Production of Recombinant Proteins 7.1. Production of Bacterial Proteins:

7.7.1. Production of Aminoglycoside 3'-phosphotransferase (I):

The expression plasmids pP4-Kan and pP4R-Kan (Example 3.1) and also the cloning plasmid pSK-Kan401 (control) were used to transform *K. lactis* yeast MW98-8C. The cells transformed with pP4-Kan and pP4R-Kan possess G418 resistance in a YPD medium (yeast extract 10 g/l; peptone 20 g/l; glucose 20 g/l) containing 2% ethanol and doses of geneticin ranging from 200 to 400 g/ml, whereas the cells transformed with plasmid pSK-Kan401 are sensitive to geneticin.

This result shows:

that the aph gene is expressed in yeasts transformed with plasmids pP4-Kan and pP4R-Kan, thereby demonstrating that the 1.2-kb fragment does indeed carry functional promoter activity, and that this fragment hence does indeed carry bidirectional promoter activity, since the aph gene is expressed in both constructions, i.e irrespective of the orientation of the 1.2-kb BamHI-BglII fragment contain the K1ADH4 promoter.

Plasmids pP4-15Kan and pP4-60Kan confer geneticin resistance on the strain MW98-8C cultured in a YPD medium containing 2% of ethanol and doses of geneticin above 200 g/ml.

These results clearly show that active derivatives of the K1ADH4promoter carried by the 1.2-kb fragment may be obtained by fragmentation. These results also confirm the bidirectional activity of this promoter.

7.1.2. Production of S-glucuronidase (FIG. 15):

Plasmids pP4-GUS and pSK-GUS (Example 3.2) were used to transform *K. lactis* strain MW98-8C (ura3 lysA argA), selecting recombinant cells for their prototrophy with respect to uracil on an SD synthetic medium (yeast nitrogen base without amino acids 0.67%, glucose 2%) supplemented with arginine (20 mg/1) and lysine (30 mg/1).

The recombinant cells were cultured to stationary phase in YPD (10 ml). The cells were then ruptured by means of glass beads in Eppendorf tubes and centrifuged, and the supernatants analysed by minigel (5% acrylamide) electrophoresis under non-denaturing conditions. The gels and buffers used have been described by Williamson et al. (Nature 283 (1980) 214–216).

Samples corresponding to 20–40 μg of proteins were separated by acrylamide gel (5%) electrophoresis. Migration was carried out at 4° C. for 60 minutes under a current of 20 mA.

β-Glucuronidase activity was demonstrated by soaking the gels in a staining solution containing 50 mM $Na_2HPO_4$ pH 7.0 and 50 g/ml of 5-bromo-4-chloro-3-indolyl glucuronide (X-Glu) in 5 mg/ml of dimethylformamide (Jefferson R.A., Plant. Mol. Biol. Report 5 (1987) 387–405). The gels were maintained at 37° C. in this solution until the bands appeared.

The results obtained are presented in FIG. 15. The gel illustrated shows clearly a band in lanes 1 to 6, corresponding to MW98-8C cells transformed with plasmid pP4-GUS, and no signal in lane C, corresponding to MW98-8C cells transformed with plasmid pSK-GUS, which does not contain a promoter region of the invention.

Moreover, cells transformed with plasmids pP4-GUS and pSK-GUS were also cultured on a YPD medium supplemented with geneticin (200 mg/l). The transformants containing pP4-GUS acquired resistance to this antibiotic, while the control strain containing pSK-GUS remains sensitive.

These results confirm the bidirectional promoter activity of the 1.2-kb fragment. They show, in addition, that this fragment may be used for the simultaneous expression of two heterologous genes, inserted on each side of the K1ADH4promoter, in the 2 opposite orientations.

7.2 Production of Mammalian Proteins:

7.2.1. Expression of the Prepro-HSA Gens Under the Control of the Whole K1ADH4 Promoter (FIGS. 16–17):

The expression plasmid pYG132 was used to transform K. lactis yeast strains MW98-8C (Rag2$^+$, incapable of producing ethanol from glucose) and CBS 293.91 (Rag2$^+$, metabolising glucose to produce ethanol). After selection of recombinant cells on YPD medium supplemented with geneticin (200 mg/l), the transformants were precultured for approximately 20 hours in Erlenmeyer flasks in an M9EL10 medium (M9 medium [Maniatis et al., cited above] supplemented with 10 g/l of yeast extract) in the presence of glucose (20 g/l) at 28° C. with agitation. This preculture was then used to inoculate, at a dilution of $10^{-3}$, 300-ml Erlenmeyers containing M9EL10 medium (50 ml) in the presence of various carbon sources (either glucose alone [20 g/l], or glucose [20 g/l] plus ethanol [20 g/l], or glycerol alone [20 g/l], or glycerol [20 g/l] plus ethanol [20 g/l]).

After culture of the recombinant cells for 5 days at 28° C. with agitation, cell-free samples of the supernatant of each culture were withdrawn and mixed with an equivalent volume of Laemmli 2x buffer (Laemmli, Nature 227 [1970] 680). After heating to 96° C. for 10 minutes, the proteins contained in an equivalent of 25 μl of supernatant were separated (25 mA) on 8.5% SDS-polyacrylamide gel. The secretion of albumin was then visualised by staining the gel with Coomassie blue, and evaluated by densitometry.

FIG. 16 shows the result obtained with the strain MW98-8C/pYG132, for which a high level of albumin secretion was observed when the cells were cultured in the presence of ethanol. In contrast, no HSA was detected in the supernatant when the cells were cultured in the presence of glucose or glycerol.

In contrast to the results obtained with the strain MW98-8C/pYG132, the transformants CBS293.91/pYG132 were capable of producing HSA under all the culture conditions mentioned above (FIG. 17). Albumin production was 2 to 3 times as high in a culture containing ethanol added to the medium, compared to a culture in which ethanol is the product of cell metabolism.

These results confirm the capacity of the host/vector systems described in the above examples for producing high levels of a recombinant protein, whether of bacterial or mammalian origin, under a condition of induction. For example, albumin production in the strain CBS 293.91/pYG132 in a medium containing glycerol or glucose in the presence of ethanol (FIG. 17) was estimatedby densitometry to be 190–200 mg/l.

These results also confirm the absence of repression of the K1ADH4 promoter by glucose, since albumin production is not reduced in the presence of the latter.

7.2.2. Expression of the Prepro-HSA Gene Under the Control of the Truncated K1ADH4 Promoter (FIG. 18):

The expression plasmid pYG130 was used to transform K. lactis strain CBS 293.91 (Rag2$^+$). After selection of recombinant cells on YPD medium supplemented with geneticin (200 mg/l), the transformants were precultured and cultured as decribed in the preceding example. Albumin secretion was evaluated by electrophoresis of samples of culture supernatants as described under 7.2.1. The result obtained with the truncated derivative of the K1ADH4 promoter is shown in FIG. 18: the host/vector system CBS293.91/pYG130 is clearly capable of producing and secreting recombinant albumin. As in the example of plasmid pYG132 (whole K1ADH4 promoter), albumin production is observed in the medium containing glucose as the sole carbon source, but at a lower level compared to the whole promoter. In contrast, culture of the cells in a medium containing glucose plus ethanol increased HSA production by a factor of 2 to 3 (FIG. 18).

One skilled in the art will readily appreciate the present invention is well adapted to carry out the objects and obtain the ends and advantages mentioned, as well as those inherent therein. The DNA sequences, recombinant DNAs, vectors, cells, methods, procedures, and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

DEPOSIT OF STRAINS USEFUL IN PRACTICING THE INVENTION

A sample of K. lactis strain 2359/152 was deposited on 4th June 1991 with the Centraalbureau voor Schimmelkulturen (CBS) at Baarn, Holland, under the conditions of the Budapest Treaty, under number CBS 289.91. K. lactis strain CBS 293.91 corresponds to the strain CBS1065 redeposited on 11th June 1991 according to the conditions of the Budapest Treaty.

TABLE 1

| VECTOR | SHUTTLE PLASMID | EXPRESSION CASSETTE |
|---|---|---|
| pP4-Kan | pSK-Kan401 | 1.2 > aph |
| pP4R-Kan | pSK-Kan401 | aph 1.2 > |
| pP4-GUS | pSK-Kan-401 | aph 1.2 > GUS |
| pYG131 | pYG404D | 1.2 > NONE |
| pYG132 | pTG404D | 1.2 > HSA |

TABLE 2

| VECTOR | SHUTTLE PLASMID | EXPRESSION CASSETTE |
|---|---|---|
| P4-15Kan | pSK-Kan401 | 0.5 > aph |
| pP4-60Kan | pSK-Kan401 | aph 0.7 |
| pYG129 | pYG404DH | 0.67 > NONE |
| pYG130 | pYG404DH | 0.67 > HSA |

TABLE 3

| Strain\Medium | Glucose | Ethanol | Glucose + Ethanol | Fructose | Glycerol |
|---|---|---|---|---|---|
| 2359/152 (Rag2+) | + | + | + | + | − |
| MW98-8C (Rag2−) | − | + | + | + | − |

We claim:

1. A DNA sequence selected from the group consisting of:
   (a) the DNA sequence presented in FIG. 1 (SEQ ID NO: 1);
   (b) the complement of the DNA sequence presented in FIG. 1 (SEQ ID NO: 1);
   (c) the DNA sequence of (a) or (b) further comprising one or more regulatory elements of activator regions; and
   (d) the DNA sequence of (a), (b) or (c) comprising one or more deletions;
   wherein said DNA sequence possesses transcriptional promoter activity.

2. The DNA sequence of claim 1 wherein said sequence is selected from the group consisting of:
   (a) the approximately 0.5 kb SacI-BamHI fragment presented in FIG. 2 (SEQ ID NO: 2);
   (b) the complement of the DNA sequence presented in FIG. 2 (SEQ ID NO: 2);
   (c) the DNA sequence of (a) or (b) further comprising one or more regulatory elements or activator regions; and
   (d) the DNA sequence of (a), (b) or (c) comprising one or more deletions;
   wherein sad DNA sequence possesses transcriptional promoter activity.

3. The DNA sequence of claim 1 wherein said sequence is selected from the group consisting of:
   (a) the approximately 0.7-kb SalI-HindIII fragment presented in FIG. 3 (SEQ ID NO: 3);
   (b) the complement of the DNA sequence presented in FIG. 3 (SEQ ID NO: 3);
   (c) the DNA sequence of (a) or (b) further comprising one or more regulatory elements or activator regions; and
   (d) the DNA sequence of (a), (b) or (c) comprising one or more deletions;
   wherein said DNA sequence possesses transcriptional promoter activity.

4. The DNA sequence of claim 1 wherein said sequence is selected from the group consisting of:
   (a) the approximately 0.7-kb BglII-SacI fragment corresponding to the fragment bounded by nucleotides 1 and 723 of the strand complementary to the sequence given in FIG. 1 (SEQ ID NO: 1);
   (b) the complement of the DNA sequence in (a);
   (c) the DNA sequence of (a) or (b) further comprising one or more regulatory elements or acttivator regions; and
   (d) the DNA sequence of (a), (b) or (c) comprising one or more deletions;
   wherein said DNA sequence possesses transcriptional promoter activity.

5. A recombinant DNA comprising the DNA sequence of claim 1 operably linked to a structural gene or genes encoding one or more heterologous proteins.

6. The recombinant DNA according to claim 5, wherein each structural gene additionally comprises a secretion signal which enables the expression product or products of said structural gene or genes to be secreted.

7. The recombinant DNA according to claim 6, wherein said structural gene or genes encode a protein selected from the group consisting of enzymes, blood derivatives, insulin, variants of insulin, lymphokines, growth factors, apolipoproteins, antigenic polypeptides for the production of vaccines, viral receptors, and fusion polypeptides comprising an active part fused to a stabilizing part.

8. The recombinant DNA according to claim 5, which forms part of an expression plasmid, wherein said expression plasmid is either autonomously replicating or integrative.

9. A recombinant cell containing a DNA sequence according to claim 5.

10. The recombinant cell according to claim 9, wherein said cell is a yeast.

11. The recombinant cell according to claim 10, wherein said yeast is of the genus Kluyveromyces.

12. The recombinant DNA according to claim 7, wherein said enzymes are selected from the group consisting of superoxide dismutase, catalase, amylases, lipases, amidases, and chymosin.

13. The recombinant DNA according to claim 7, wherein said blood derivatives are selected from the group consisting of serum albumin, molecular variants of serum albumin, alpha-globin, beta-globin, factor VIII, factor IX, von Willebrand factor (vWF), biologically active fragments of vWF, fibronectin and 1-alpha-antitrypsin.

14. The recombinant DNA according to claim 7, wherein said lymphokines are selected from the group consisting of the interleukins, interferons, and colony stimulation factors.

15. The recombinant DNA according to claim 14, wherein said colony stimulation factors are selected from the group consisting of G-CSF, GM-CSF, M-CSF, TNF, and TRF.

16. The recombinant DNA according to claim 7, wherein said growth factors are selected from the group consisting of growth hormone, erythropoietin, FGF, EGF, PDGF, and TGF.

17. The recombinant DNA according to claim 7, wherein said antigenic polypeptides are selected from the group consisting of antigens from hepatitis, cytomegalovirus, Epstein-Barr, and herpes.

18. A process for the preparation of a recombinant protein by expression of its gene in a cellular host comprising:
   (a) expression of said gene under the control of a sequence according to claim 1, and
   (b) recovering the recombinant protein.

19. The method of claim 18, wherein said protein is selected from the group consisting of enzymes, blood derivatives, insulin, variants of insulin, lymphokines, growth factors, apolipoproteins, antigenic polypeptides for the production of vaccines, viral receptors, and fusion polypeptides comprising an active pa fused to a stabilizing part.

20. The method according to claim 18, wherein said protein is human serum albumin or a molecular variant thereof.

21. The process according to claim 18 further comprising simultaneous expression of recombinant genes, wherein said promoter is bidirectional and said genes are inserted on each side of the promoter, in the two opposite orientations.

22. The method according to claim 19, wherein said enzymes are selected from the group consisting of superoxide dismutase, catalase, amylases, lipases, amidases, and chymosin.

23. The method according to claim 19, wherein said blood derivatives are selected from the group consisting of serum albumin, molecular variants of serum albumin, alpha-globin, beta-globin, factor VIII, factor IX, von Willebrand' factor (vWF), biologically active fragments of vWF, fibronectin and 1-alpha-antitrypsin.

24. The method according to claim 19, wherein said lymphokines are selected from the group consisting of the interleukins, interferons, and colony stimulation factors.

25. The method according to claim 24, wherein said colony stimulation factors are selected from the group consisting of G-CSF, GM-CSF, M-CSF, TNF, and TRF.

26. The method according to claim 19, wherein said growth factors are selected from the group consisting of growth hormone, erythropoietin, FGF, EGF, PDGF, and TGF.

27. The method according to claim 19, wherein said antigenic polypeptides are selected from the group consisting of antigens from hepatitis, cytomegalovirus, Epstein-Barr, and herpes.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1211 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Kluyveromyces lactis ( x i ) SEQUENCE DESCRIPTION: SEQ ID NO:1:

```
AGATCTATCA  ACGGCTACTA  ATAGAAGTTC  AACACCCAGA  AATTGATTGT  TTTGGCCTGA     60
AATGTTAATG  GCAGGGAATC  AAGTATGAAG  TATGAAGTAT  GAAGTGTGAA  GTGTGAATCC    120
CGTAAAATCG  GAGAAACATG  TGGTCACCTG  GTCAAGGACT  TAAGGGAACA  CAGCGGTTGT    180
TCTCGGCATT  AAGCGGTACT  ATTGTCACTT  TGTAATGGCA  GTCCGAATCA  CGTTTTATTA    240
TATGGGGGGG  GGGAAGGAAC  GACGGTACAT  AAGAATGAGG  GGCTTGGTTG  CGGTGTACGG    300
GTTAGTACC   CCTCTCGTCC  GTGCAAGCCC  AAAGACAAGT  TTTGTTTCT   TTTCGTATC     360
CATCCCCAGA  ACAGTGCGCA  GCAAGGAAAT  ATTCCGTCAT  GCGTTTGGAT  GGTTTTTCCC    420
CTATTGAGGG  GCAAGTGAGG  GGTAAACGAA  CGGCGCCTGA  AATTTTCCCG  CTCAATGATA    480
TGAATAATCA  GTAGGATCTC  CGAGTTTCGC  AAGAAGCAGT  AAGCAACTCC  GTTTATTGC     540
GAGACAACAC  TATTGTGAGA  AAAGGCACTC  AAAAAGCGAC  CTCCGTTAAT  TGATGTCAAC    600
TGGCATCAAT  TTGAGATACT  TTGGGTCAAT  TTGCAGTGTG  CATTCGCATT  CTTTGTGTTA    660
AAATCCTTTT  CCCCAGAAGT  CGGAGTTTAC  AGGACACAGG  GTGTGGAGCA  ATTGGGAGAG    720
CTCCAGCAGG  GCTGGAGCTC  TGCCTCTGCC  TCTGCCCCAG  GTCCAGGTCC  AAGTCCAAGT    780
CCAGGTCCAG  CGAGAACCGG  AGTGAGAGGT  GTGTGCTGTG  CCTTCCACTA  AACGAACCAG    840
TATCCCAGGT  CTCTTAAGTT  TCCCAAATCT  CGGCATGGTC  AGGCCTCTCC  ACTGTAGCAG    900
CCGCAGCACA  TTTTTTTTT   TTTTCTCTCT  TCTAATGGAT  CAAGCATCAC  TACTTATCAC    960
AATTTATCAC  TTTTCCAAT   GATGTTGCCA  TTGCCCTTGT  TGGCCTTCTC  GAACTAGTCC   1020
GTCTTTCTGG  TTTAACTTGG  TGAGGGAAAT  TCTTAGCACT  GGACTGCGCT  GTGATATGAC   1080
CTGTTAAATT  ATAACAAGGA  GTCGTTTTTC  AATTGACAAT  TTCTTATCAT  TGTCTCTGGG   1140
ATCAATTGGT  TTTTCTTCCT  CTCTTTCGCT  TTTCTCCCCC  ACCAACAACA  CAACATACAA   1200
```

CACACGCAAT G                                                                                                    1211

( 2 ) INFORMATION FOR SEQ ID NO:2:

( i ) SEQUENCE CHARACTERISTICS:
        ( A ) LENGTH: 464 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Kluyveromyces lactis ( x i ) SEQUENCE DESCRIPTION: SEQ ID NO:2:

```
GAGCTCTGCC   TCTGCCTCTG   CCCCAGGTCC   AGGTCCAAGT   CCAAGTCCAG   GTCCAGCGAG      60
AACCGGAGTG   AGAGGTGTGT   GCTGTGCCTT   CCACTAAACG   AACCAGTATC   CCAGGTCTCT     120
TAAGTTTCCC   AAATCTCGGC   ATGGTCAGGC   CTCTCCACTG   TAGCAGCCGC   AGCACATTTT     180
TTTTTTTTTT   CTCTCTTCTA   ATGGATCAAG   CATCACTACT   TATCACAATT   TATCACTTTT     240
TCCAATGATG   TTGCCATTGC   CCTTGTTGGC   CTTCTCGAAC   TAGTCCGTCT   TTCTGGTTTA     300
ACTTGGTGAG   GGAAATTCTT   AGCACTGGAC   TGCGCTGTGA   TATGACCTGT   TAAATTATAA     360
CAAGGAGTCG   TTTTTCAATT   GACAATTTCT   TATCATTGTC   TCTGGGATCA   ATTGGTTTTT     420
CTTCCTCTCT   TTCGCTTTTC   TCCCCACCA    ACAACACAGG   ATCC                       464
```

( 2 ) INFORMATION FOR SEQ ID NO:3:

( i ) SEQUENCE CHARACTERISTICS:
        ( A ) LENGTH: 666 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Kluyveromyces lactis ( x i ) SEQUENCE DESCRIPTION: SEQ ID NO:3:

```
GTCGACGCGA   GACAACACTA   TTGTGAGAAA   AGGCACTCAA   AAAGCGACCT   CCGTTAATTG      60
ATGTCAACTG   GCATCAATTT   GAGATACTTT   GGGTCAATTT   GCAGTGTGCA   TTCGCATTCT     120
TTGTGTTAAA   ATCCTTTTCC   CCAGAAGTCG   GAGTTTACAG   GACACAGGGT   GTGGAGCAAT     180
TGGGAGAGCT   CCAGCAGGGC   TGGAGCTCTG   CCTCTGCCTC   TGCCCCAGGT   CCAGGTCCAA     240
GTCCAAGTCC   AGGTCCAGCG   AGAACCGGAG   TGAGAGGTGT   GTGCTGTGCC   TTCCACTAAA     300
CGAACCAGTA   TCCCAGGTCT   CTTAAGTTTC   CCAAATCTCG   GCATGGTCAG   GCCTCTCCAC     360
TGTAGCAGCC   GCAGCACATT   TTTTTTTTTT   TTCTCTCTTC   TAATGGATCA   AGCATCACTA     420
CTTATCACAA   TTTATCACTT   TTTCCAATGA   TGTTGCCATT   GCCCTTGTTG   GCCTTCTCGA     480
ACTAGTCCGT   CTTTCTGGTT   TAACTTGGTG   AGGGAAATTC   TTAGCACTGG   ACTGCGCTGT     540
GATATGACCT   GTTAAATTAT   AACAAGGAGT   CGTTTTTCAA   TTGACAATTT   CTTATCATTG     600
TCTCTGGGAT   CAATTGGTTT   TTCTTCCTCT   CTTTCGCTTT   TCTCCCCCAC   CAACAACACA     660
AAGCTT                                                                         666
```

( 2 ) INFORMATION FOR SEQ ID NO:4:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

CTCCCCCACC AACAACACAA CATACAACAC ACGCAATGTT CAGATT    46

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

CTCCCCCACC AACAACACAG GATCCAACAC ACGCAATGTT CAGATT    46

( 2 ) INFORMATION FOR SEQ ID NO:6:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

AATCTGAACA TTGCGTGTGT TGGATCCTGT GTTGTTGGTG GGGGAG    46

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GAAATGCATA AGCTCTTGCC ATTCTCACCG    30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

GGGGTCGACG CGAGACAACA CTATTGTGAG    30

( 2 ) INFORMATION FOR SEQ ID NO:9:

( i ) SEQUENCE CHARACTERISTICS:
        ( A ) LENGTH: 28 base pairs
        ( B ) TYPE: nucleic acid (C) STRANDEDNESS: single
(D) TOPOLOGY: linear (ii) MOLECULE TYPE: other nucleic acid (xi) SEQUENCE DESCRIPTION: SEQ ID NO:9:

GGGAAGCTTT GTGTTGTTGA TGGGGGAG                                       2 8